(12) United States Patent
Ziran et al.

(10) Patent No.: US 7,867,426 B2
(45) Date of Patent: Jan. 11, 2011

(54) METHOD OF FORMING A TEMPORARY IMPLANT

(76) Inventors: Bruce H. Ziran, 686 Saddlebrook Dr., Boardman, OH (US) 44512; Joseph W. Whiteside, 3267 Olde Winter Trail, Poland, OH (US) 44514

( * ) Notice: Subject to any disclaimer, the term of this patent is extended or adjusted under 35 U.S.C. 154(b) by 249 days.

(21) Appl. No.: 11/716,757

(22) Filed: Mar. 12, 2007

(65) Prior Publication Data
US 2007/0222114 A1    Sep. 27, 2007

Related U.S. Application Data

(60) Provisional application No. 60/785,259, filed on Mar. 23, 2006.

(51) Int. Cl.
*B29C 45/14* (2006.01)
(52) U.S. Cl. .............. 264/279; 623/901; 249/61; 249/55; 249/141; 249/168
(58) Field of Classification Search .......... 264/279; 623/901; 249/61, 55, 141, 168
See application file for complete search history.

(56) References Cited

U.S. PATENT DOCUMENTS

| | | | | |
|---|---|---|---|---|
| 5,658,516 A | * | 8/1997 | Eppley et al. | 264/251 |
| 5,997,582 A | * | 12/1999 | Weiss | 606/89 |
| 6,155,812 A | * | 12/2000 | Smith et al. | 425/318 |
| 6,361,731 B1 | | 3/2002 | Smith et al. | |
| 6,561,783 B2 | * | 5/2003 | Hsu | 425/132 |
| 6,656,143 B2 | * | 12/2003 | Browd | 602/13 |
| 6,942,475 B2 | | 9/2005 | Ensign et al. | |
| 2003/0021861 A1 | * | 1/2003 | Yamada | 425/308 |
| 2005/0119756 A1 | | 6/2005 | Soffiati | |

\* cited by examiner

*Primary Examiner*—Joseph S Del Sole
*Assistant Examiner*—John P Robitaille
(74) *Attorney, Agent, or Firm*—Gary P. Topolosky; Robert J. Herberger

(57) ABSTRACT

A mold assembly and method of forming a surgical implant from bone cement. The method has the steps of connecting a plurality of mold segments to approximate the size of a patient implant. Each mold segment has an open channel. The method may further include aligning the channels of connected mold segments, positioning a centralizing holder on a reinforcement member, mixing bone cement, pouring at least some bone cement through the channels and into connected mold segments, fitting the reinforcement member into the mold segments, curing the bone cement; and removing the cured surgical implant.

14 Claims, 27 Drawing Sheets

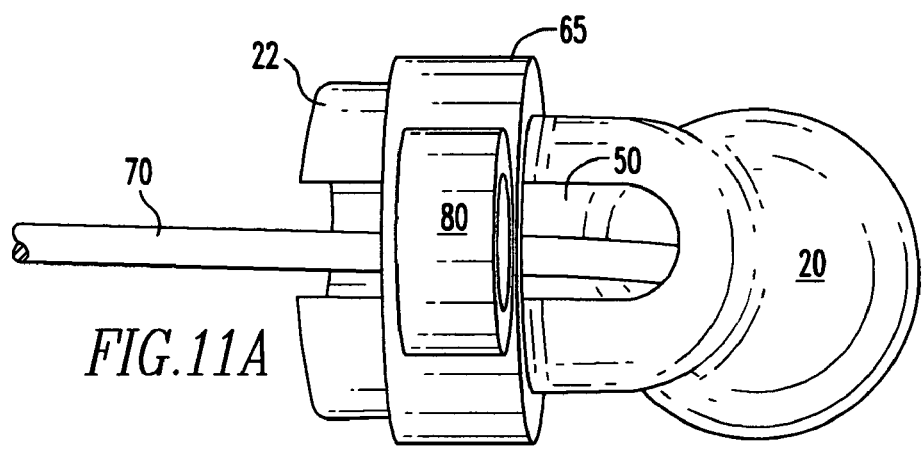
FIG.11A
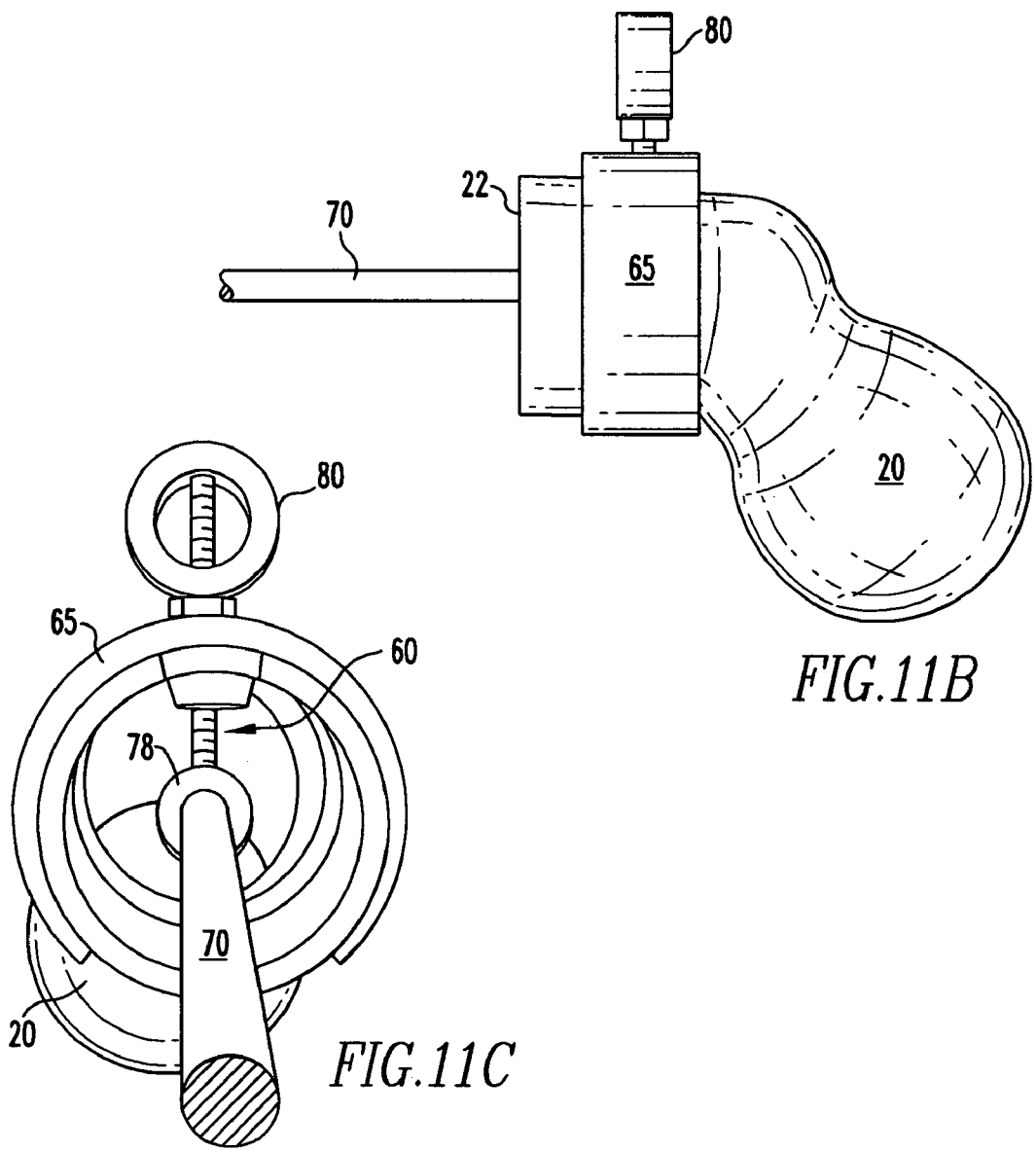
FIG.11B
FIG.11C

METHOD OF FORMING A TEMPORARY IMPLANT

CROSS-REFERENCE TO RELATED APPLICATIONS

This application claims the benefit of priority to U.S. Provisional Application Ser. No. 60/785,259, filed on Mar. 23, 2006 and fully incorporated by reference herein.

FIELD OF THE INVENTION

The present invention relates generally to implants for use in orthopedic surgical procedures and more particularly, to a method of forming temporary implants for such procedures. This invention further relates to a mold system for making such temporary implants.

BACKGROUND OF THE INVENTION

Joint arthroplasty involves replacing articular cartilage with an implant that is intended to last as long as possible. The most common joints to replace are the knee and hip. Elbow and humerus replacements are the next most common. While it may be possible to also replace wrist and ankle bones with such an implant, are also possible to replace with an implant, effective treatments by fusion are still accepted and preferred by doctors and patients.

Initially reserved for patients suffering from arthritic conditions, hip and knee replacements have become increasingly popular especially for younger, more active individuals. As more of the "baby boomer" population requires joint arthroplasty, need for treating fractures and other joint conditions of the elderly will nearly double. There is also a growing secondary market for revision surgery products. The latter surgery carries a higher complication risk due to decreasing functional status of the patient with each intervention and with higher occurrences of infection, in part, due to the usual multi-stage nature of such surgeries and due to the fact that an antibiotic regimen alone is usually insufficient for curing same. Many of these infections are due to the general behavior of biofilm bacteria, i.e., the pathologic organisms that form colonies on inert surfaces. The best treatment for such situations is a total purging/removal of the infected area.

Joint replacements, being made of an inert material, provide excellent surfaces on which bacteria may colonize. Once a joint gets infected, general treatment involves completely removing the prior implant (itself, a rather risky procedure), followed by wide, local debridement of adjacent tissues until the wound bed consists of only healthy, "non-inert", i.e., living with good blood flow, tissue. Then, both systemic and local antibiotic depots can be used to further treat the patient, mostly for guarding against remaining or new bacteria. Once the tissue bed is clean, a re-implantation of the joint/body part can be performed with hopes that a bacterial infection does not return.

Some procedural difficulties encountered with the aforementioned approach include maintaining the soft tissue envelope during the treatment period. Since there is a loss of axial stability by virtue of removing a joint, the soft tissues can contract and shorten. That in turn, makes the re-implantation process very difficult and risky. If the soft tissue tension can be maintained and, even better, if axial stability with a functional spacer can be used, then the patient minimizes functional loss and re-implantation is facilitated and safer. Furthermore, to minimize the potential for colonization of the intervening spacer, antibiotics can be added to help prevent colonization. Antibiotic bone cement has been used as a treatment of infections for a long time since the work of Bucholz. Since then, there has been developed an antibiotic laden, bone cement as well as products in pre-fabricated shapes that contain a single antibiotic. These existing products contain an aminoglycoside which effectively helps prevent and fight bacterial colonization.

Another method for local antibiotic delivery involves making "beads" or using a powdered, heat stable antibiotic mixed with a common bone cement like poly-methyl-methacrylate (or PMMA), before being formed into small beads on a wire or string. That string of antibiotic beads then gets packed into the wound for eluting high concentrations of antibiotic over time. While effective for infection, that known method provides no limb support for a patient otherwise unable to support their own weight thus rendering such patients wheelchair or bed bound during treatment and recovery.

Another problem previously mentioned is the natural tension of soft tissue to shorten and/or scar a limb. This shortening is difficult to counteract during some re-implantations. There is an increased risk of intra-operative complications and potential neurovascular injury. To deal with this issue, surgeons and manufacturers have created a temporary prosthetic made from an antibiotic laden, bone cement. Representative examples of hip and/or knee implant prosthetics are shown and described in Smith et al U.S. Pat. Nos. 6,155,812 and 6,361,731.

An alternative family of temporary prosthetics is commonly known as a Prostalac® device. For a typical Prostalac hip replacement, a small metal inner core is manually surrounded with antibiotic-laden PMMA. This device provides a metal mold into which a core prosthesis is placed and surrounded with antibiotic laden bone cement. While a surgeon may use the Prostalac for custom blending a preferred recipe of antibiotics, the resultant prosthetic product is cumbersome, expensive to manufacture and rather difficult to use. In any event, a prosthesis is still required and there is little expectation of applicability beyond a simple hip substitution, i.e., those not having extensive proximal femoral bone loss. The same would be true for any intended adaptations of a Prostalac-type system for knee, elbow and/or shoulder replacements (currently not available in the United States).

Yet another alternative to the Prostalac product is a device sold by Tecres as described in Soffiati U.S. Published Application No. 2005/0119756. That device gets delivered to a surgeon pre-fabricated. As such, the antibiotic contents in a Tecres product cannot be modulated, or otherwise customized for a given patient. Due to its limited variety of available sizes, the Tecres knee and hip units do not fit every patient. Nor do they provide axial or rotational stability. This is especially true when a smaller sized stem gets implanted in a larger femoral canal. The attending surgical staff has the option of hand mixing bone cement to manually form a collar (or other adapter over the pre-made Tecres). But such retrofitting takes up valuable staff time and energies, defeating the otherwise beneficial advantages of a system of pre-fabricated parts.

A Biomet® Stage One system, and the somewhat similar process of Ensign et al U.S. Pat. No. 6,942,475, offer disposable knee mold shells, but only the shell parts. Even though these products accomodate custom antibiotic tailoring, they offer limited sizes of knee parts. Their hip component is only intended to replace the femoral neck and head. It uses a standard stem. It is not able to replace diaphyseal parts and only comes in limited sizes for the head. Thus, the options for this system are limited and do not provide for "custom spacers".

Today's surgeons desire a product that allows for custom fitting for the needs of every implant patient; one that can be expanded in situ (i.e., in the operating room) for accommodating surgical "surprises" like the need to remove additional adjacent bone and/or partially expand a region of the implant for enhancing stability in the canal region. Such a product should be adaptable for making a variety of body part shapes, i.e. for an implant for the ankle, elbow, etc. The method for making such implants from PMMA (or other bone cements) should: (a) enable a wide range of antibiotic recipes, and (b) be cost effective to make and use in situ (i.e. in the operating room itself); so as to lend itself toward ready disposability.

The present device differs from all others in that the sizes for same are templated from non-implanted trials, similar to those used during sizing for joint replacement. Once the patient's size is determined, the corresponding mold is chosen and used to fabricate a cement spacer. Furthermore, by virtue of its modularity, the device can create metaphyseal and diaphyseal components so that greater bone losses can be accommodated. It is unlike the Biomet mold system in that a port is not used. Rather, the present invention introduces cement through an open channel. And while it uses a biocompatible plastic mold that is completely removed and discarded like other products, the molds for this invention are modular and completely customized. This device can be customized in discrete size intervals. It is modular so that if needed, an entire bone segment can be fabricated. In order to maintain strength, an internal steel core can be placed by the surgeon as "rebar" to increase strength. The manufacturing process, materials, and sterilization process all use existing and accepted materials and methods. It will not leach into the mold and does not come into direct contact with the patient. It is much easier to use than other products due to its method of design, and will require a minimum of post-fabrication modifications.

This invention also has potential uses in diaphyseal bone loss cases, i.e., where a segment of bone is lost due to trauma. In such cases, the subsequent layer of tissue surrounding the spacer has living cells that can participate in the subsequent reconstructive process of healing. We are not aware of any other device that provides such modularity, ease of use, and variety of application.

SUMMARY OF THE INVENTION

In accordance with teachings of this invention, there is described a mold assembly and method of forming a temporary surgical implant from bone cement. The method comprises connecting a plurality of mold segments to approximate the size of the patient implant needed with each segment having an open channel. The channels of connected mold segments are aligned and a reinforcement member on a centralizing holder positioned through the channels and into the mold segments. After bone cement is mixed, at least some cement is poured through the open channels and into the connected mold segments. If desired, a reinforcement member may then be fully fitted into the mold segments before additional bone cement is poured thereabout. Once the mold segments are substantially filled, as may be indicated by direct viewing of cement at the surface of the open channel, or via cement passing through small apertures in critical mold filling areas, the mold is steadily held in place until the cement cures. The cured cement is removed form the mold and a temporary hip, knee or other bone implant results. The mold itself is primarily opaque and unlike other devices. No ports, or small apertures opening are used in larger cavity areas. In the present invention, the open channel makes for an open vessel structure that allows free viewing into the mold cavity.

The method and mold system of this invention are customizable, unlike other devices. They provide temporary implant parts, in a plurality of sizes, to fit most every patient situation and to replace as much or as little debrided bone as the surgeon desires to remove. Unlike the pre-fabricated, limited size parts of the prior art, this method can be completely customized to each patient size. Furthermore, unlike those devices with pre-determined antibiotic mixtures, the surgeons may, if they so desire, mix their own combination of antibiotics. As such, the antibiotic combination and concentrations can be tailored to the needs determined in the clinical setting. As the primary purposes of prior art has been to inhibit colonization on the surface, this device would provide similar action, but in a much more specific and surgeon determined fashion, while considering the patient's existing allergy conditions/tolerances. The reinforcement member holder/spacer can be constructed from various mold parts, but is preferably adjustable relative to the reinforcement member it holds for keeping all of such reinforcement member surrounded by bone cement in the final temporary bone implant end product.

Using a series of trial devices, the surgical team determines the dimensions of a patient's bone defect before selecting the appropriate size mold segments to assemble together. For instance, in the accompanying drawings, both a large and small femoral knee segment are shown. For the hip, a trial would determine the head size, body size, and stem size. For example, the head could be about 58 mm, the body about 20 mm, and the stem, a long stem variety about 15 mm in diameter. This would be determined by assembling such trials and temporarily placing them into the patient. The surgeon would determine the suitability of the fit, e.g. stability and length. Such trials would dictate the mold for the final spacer.

For a hip in accordance with one particular embodiment of this invention, three pieces would be chosen and assembled together. The mold would have a hip head segment, an intermediate connector segment and a lower mold stem segment. For a smaller sized patient, the method of this invention can conceivably accommodate a two piece mold, i.e., with a hip head segment connected immediately adjacent a lower stem segment. Alternatively, should a greater amount of bone need to be debrided, multiple sections of connector mold segments may be joined together, between hip head and lower stem, for making longer temporary bone implants for a patient's immediate, prosthetic needs.

For the central reinforcement member, an appropriately sized section of metal bar is cut. For some applications, this bar or "rebar" can be precurved to better fit in a series of hip mold segments or the like. Then, using the preferred member centralizing (or holding) methods and other mold assembly steps described below, the whole mold assembly can be held in place by, for example, insulated vacuum packing, and a premixed quantity of PMMA or other bone cement poured in.

The present method accommodates several sizes of femoral head circumferences. With segmentation, attending surgeons have the luxury of fitting patients with a variety of lower bone stem sizes (i.e. diameters AND lengths) and shapes. Similarly, for the knee, the method and mold system of this invention allow surgical teams to build customized replacement body parts that have a method of constraint. As such, the risk of separation (i.e. dislocation) between femoral and tibial knee implants are reduced. Since all of the mold segments are modular and interchangeable, the entire skeleton can be "built" with said assembly. Thus, the knee and tibia, down to the ankle can be manufactured in the operating room proper. And because of the uniformity in mold segment manufacturing, and relative costs for same, the method of this invention will further encourage "one time" usage of mold segments, further eliminating the need for cleaning and re-sterilization of mold parts otherwise marked for reuse.

BRIEF DESCRIPTION OF THE DRAWINGS

Still other advantages of the present invention will become apparent to those skilled in the art after reviewing the detailed description that follows made with reference to accompanying drawings in which:

FIG. 1b is a right side, schematic view of the fully assembled hip mold from FIG. 1a;

FIG. 3a is a top schematic view of the hip head segment for the hip mold of FIG. 1a;

FIG. 11a is a top schematic view of a hip head segment with a reinforcement member and one segment joinder clip thereon;

FIG. 11b is a right side schematic view of the FIG. 11a hip head segment, reinforcement member and one segment joinder clip;

FIG. 11c is a rear axial schematic view of the FIG. 11a hip head segment, reinforcement member and one segment joinder clip;

FIG. 14b is a left side schematic view of the fully assembled, large femoral knee mold from FIG. 14a;

FIG. 14c is a front axial schematic view of the fully assembled, large femoral knee mold from FIG. 14a;

FIG. 15b is a front axial schematic view of a large femoral knee segment for comparing with smaller knee segment at FIG. 15a;

FIG. 16b is a rear axial schematic view of the large femoral knee segment for comparing with its smaller knee equivalent at FIG. 16a;

FIG. 18b is a top schematic view of a large femoral knee mold segment with a reinforcement member laid in for generally comparing with the smaller segment at FIG. 18a;

FIG. 21b is a right side schematic view of the tibial knee mold from FIG. 21a;

FIG. 21c is a slightly tilted, rear axial schematic view of the tibial knee mold from FIG. 21a;

FIG. 22b is a right side schematic view of the stemmed, tibial knee segment from FIG. 22a;

FIG. 24b is a side schematic view of the same knee segment reinforcement member holder as in FIG. 24a;

FIG. 24c is a slightly angled, bottom perspective schematic of the tibial knee segment reinforcement member holder from FIG. 24a;

FIG. 25b is a side schematic view of a the reinforcement member and reinforcement member holder from FIG. 25a;

DETAILED DESCRIPTION OF PREFERRED EMBODIMENTS

Figure 1A:
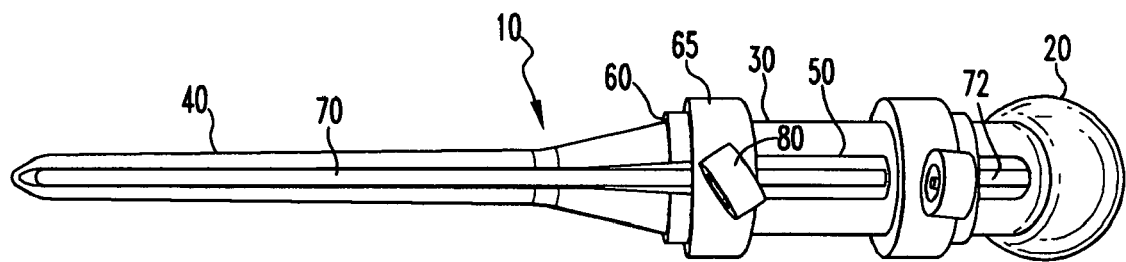
FIG. 1a is a top schematic view of a fully assembled hip implant mold according to a first preferred embodiment of the present invention.
Figure 1B:
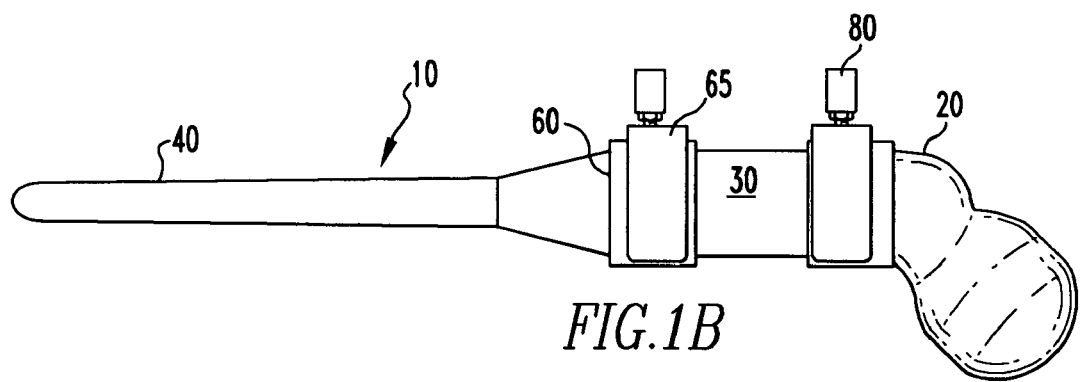
Figure 2A:
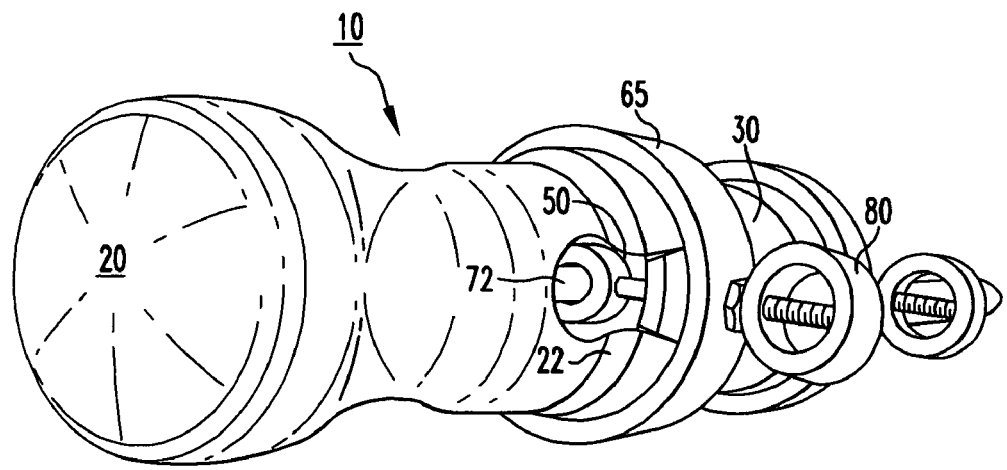
FIG. 2a is a front axial schematic view of the FIG. 1a hip mold.
Figure 2B:
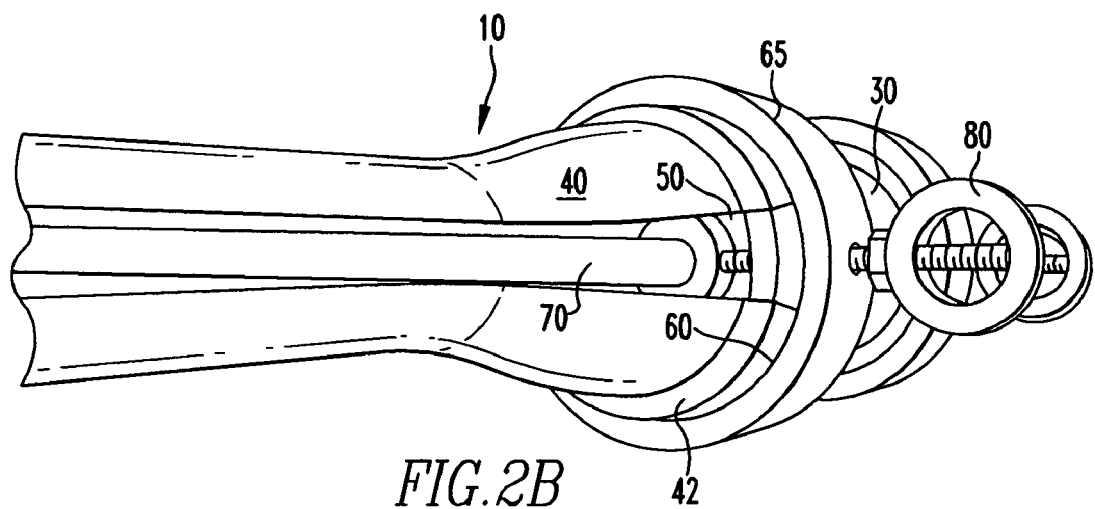
FIG. 2b is a rear axial schematic view of the FIG. 1a hip mold.
Figure 3A:
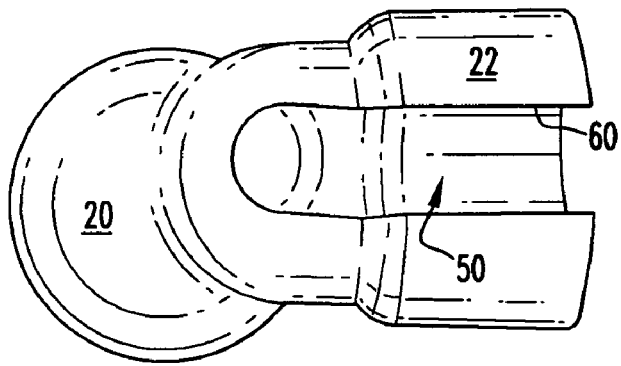
Figure 3B:
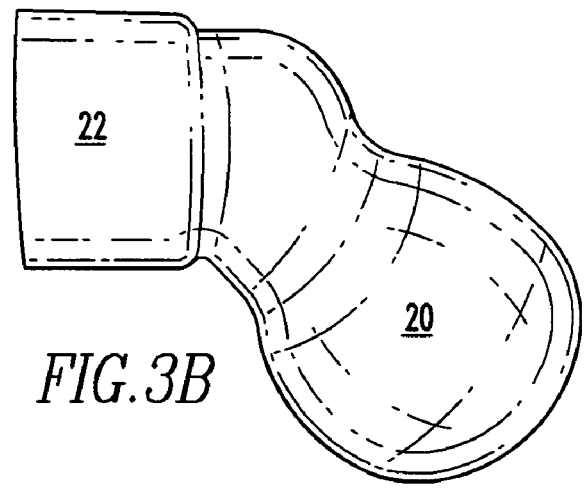
FIG. 3b is a right side schematic view of the FIG. 3a hip head segment.
Figure 3C:
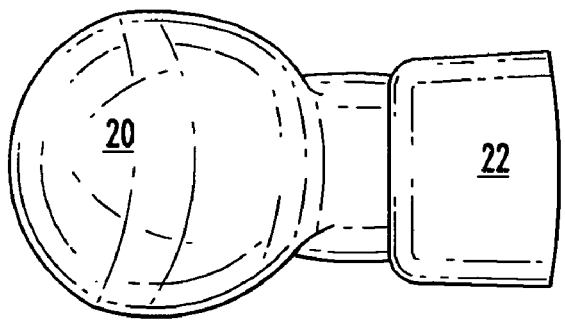
FIG. 3c is a bottom schematic view of the FIG. 3a hip head segment.
Figure 4A:
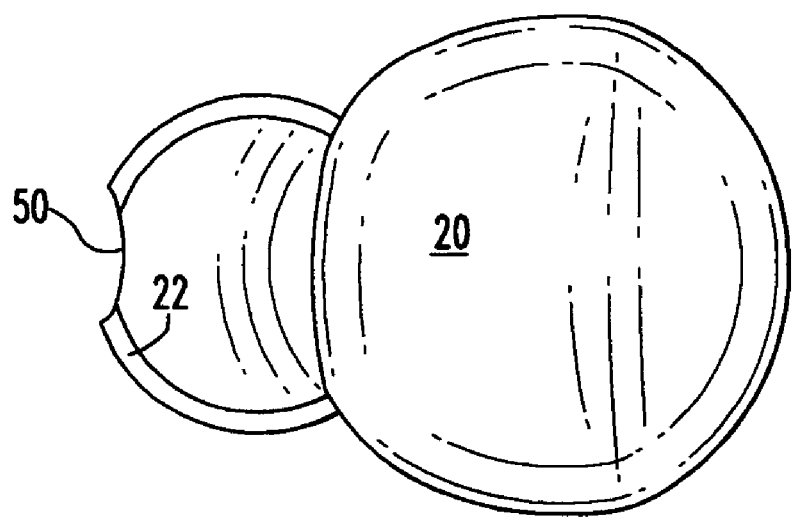
FIG. 4a is a front axial schematic view of the FIG. 3a hip head segment.
Figure 4B:
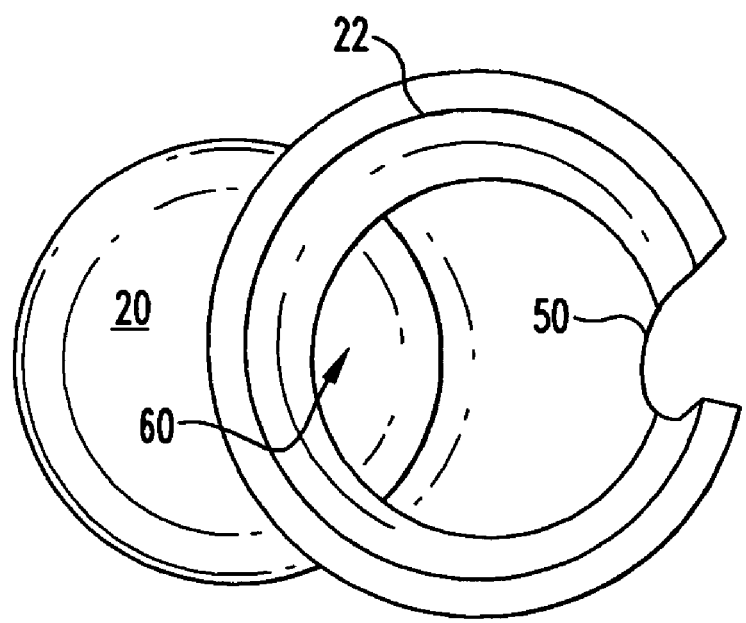
FIG. 4b is a rear axial schematic view of the FIG. 3a hip head segment.
Figure 5A:
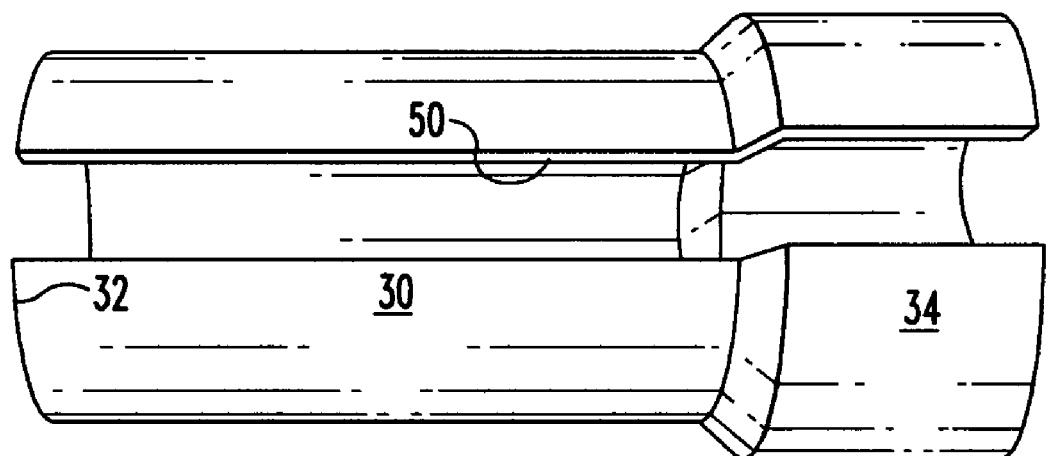
FIG. 5a is a top schematic view of a connector segment for the FIG. 1a hip mold.
Figure 5B:
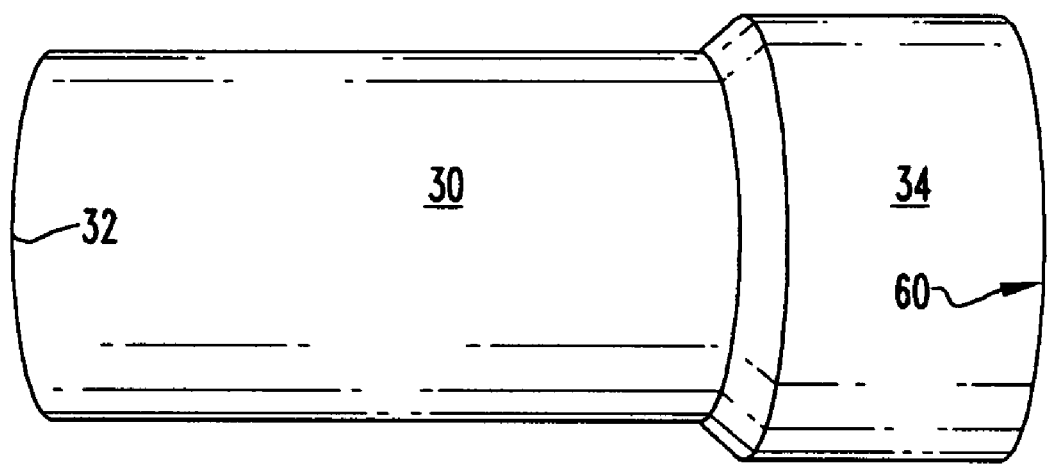
FIG. 5b is bottom schematic view of the FIG. 5a connector segment.
Figure 6A:
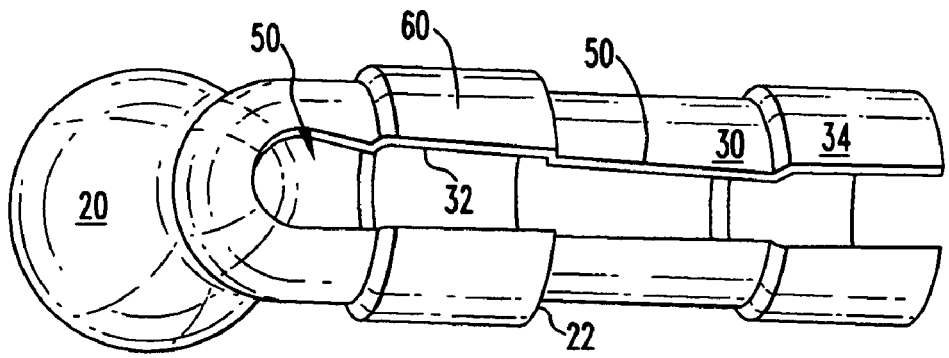
FIG. 6a is a top schematic view of s hip head and connector segment joined together.
Figure 6B:
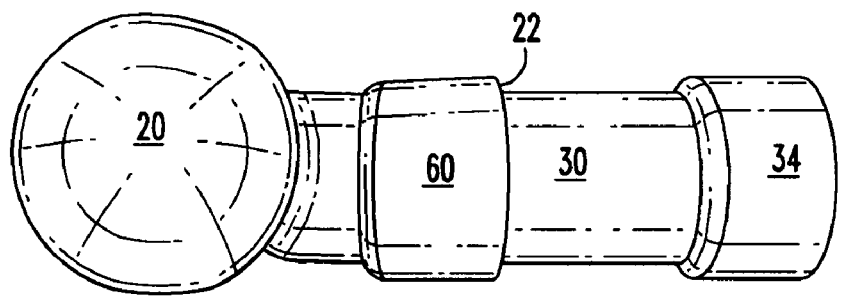
FIG. 6b is a bottom schematic view of the FIG. 6a joined hip head and connector segments.
Figure 6C:
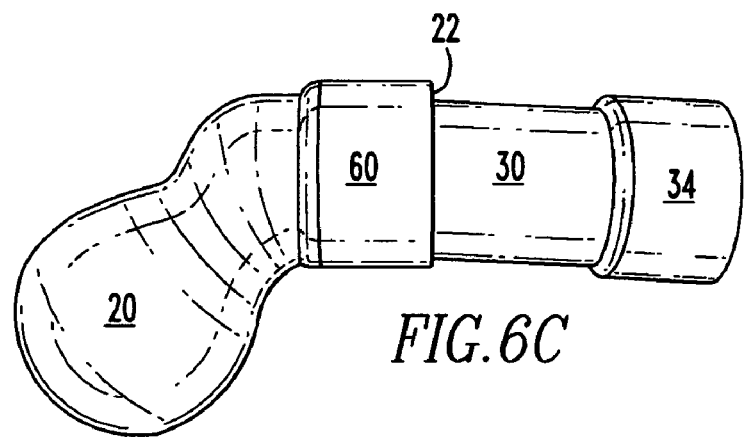
FIG. 6c is a left side schematic view of the FIG. 6a joined hip head and connector segments.
Figure 7A:
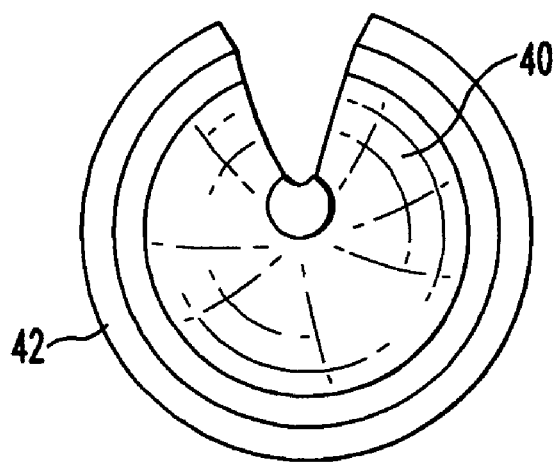
FIG. 7a is a front axial schematic view of the stem segment for the FIG. 1a hip mold.
Figure 7B:
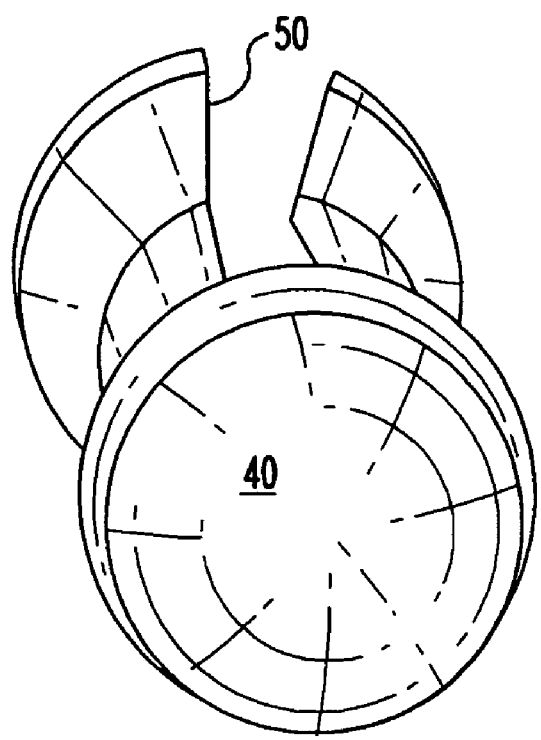
FIG. 7b is a rear axial schematic view of the FIG. 7a stem segment.
Figure 8A:
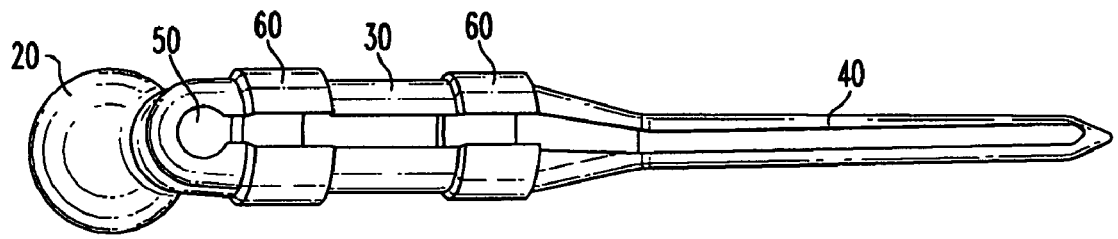
FIG. 8a is a top schematic view of the hip head, connector and stem segments which, when joined together, make up the exterior shell for the FIG. 1a hip mold.
Figure 8B:
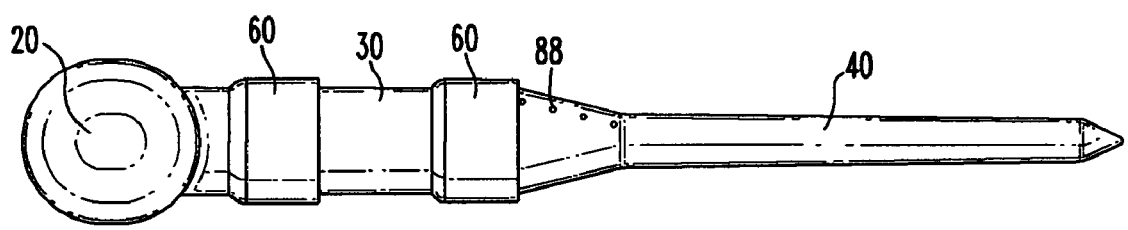
FIG. 8b is a bottom schematic view of the FIG. 8a hip head, connector and stem segments.
Figure 8C:
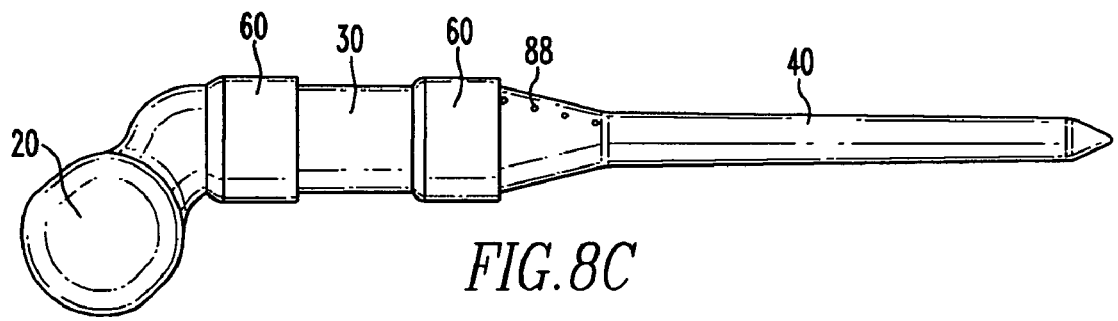
FIG. 8c is a left side schematic view of the FIG. 8a hip head, connector and stem segments.
Figure 9A:
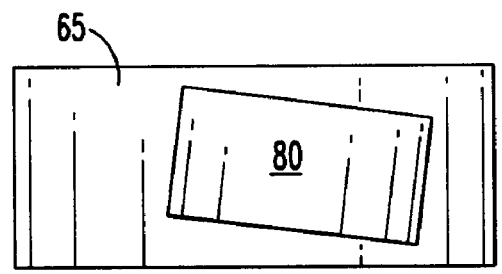
FIG. 9a is a top schematic view of a segment joinder clip and reinforcement member holder according to one embodiment of the present invention.
Figure 9B:
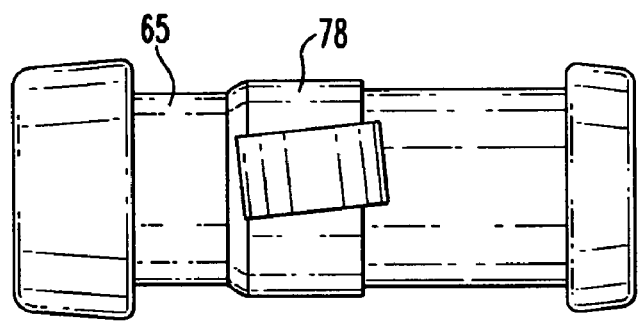
FIG. 9b is a bottom schematic view of the FIG. 9a segment joinder clip and reinforcement member holder.
Figure 9C:
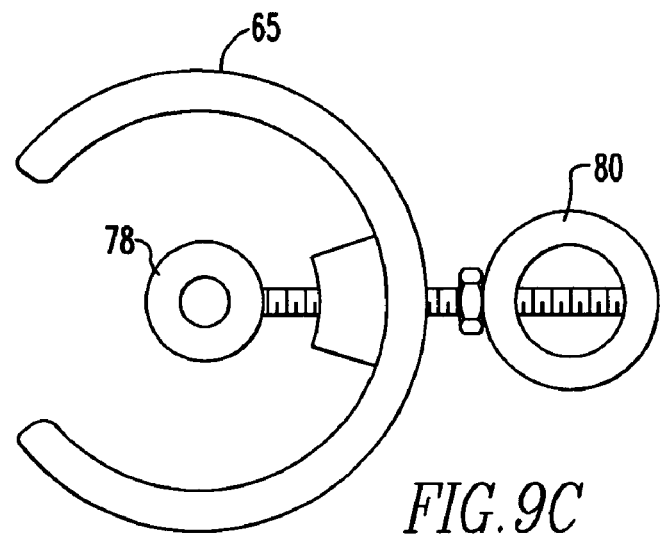
FIG. 9c is a side view of the FIG. 9a segment joinder clip and reinforcement member holder.
Figure 10A:
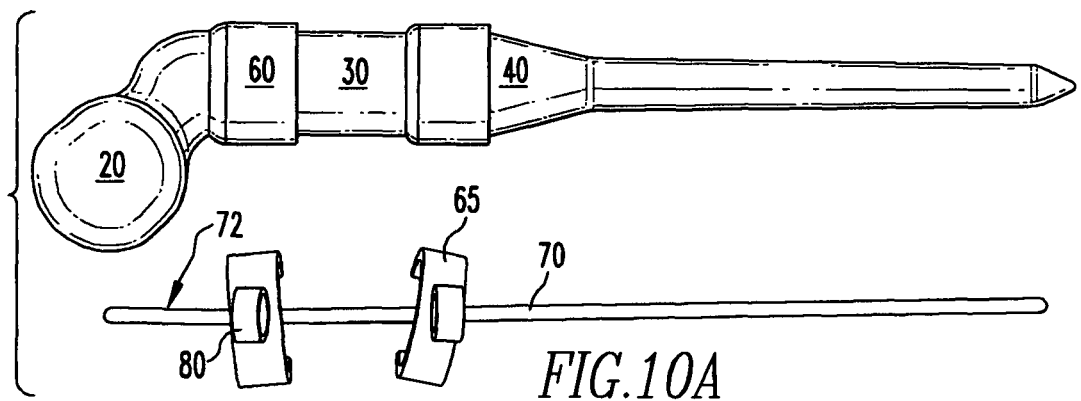
FIG. 10a is a top schematic view of two segment joinder clips on a reinforcement member positioned beneath joined hip head, connector and stem segments.
Figure 10B:
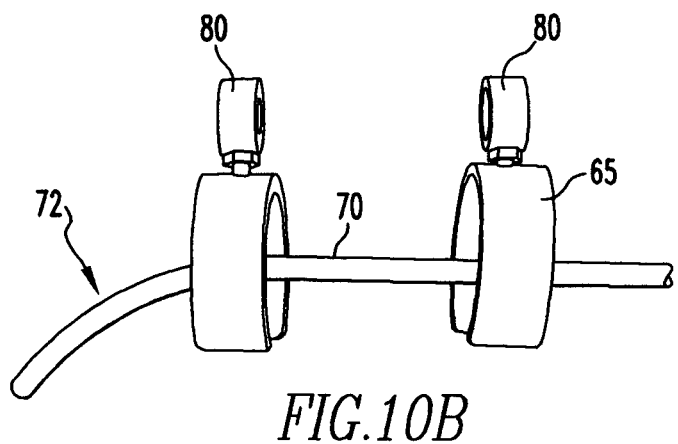
FIG. 10b is a close up, side schematic view showing the curved end to a hip mold reinforcement member with two segment joinder clips thereon.
Figure 10C:
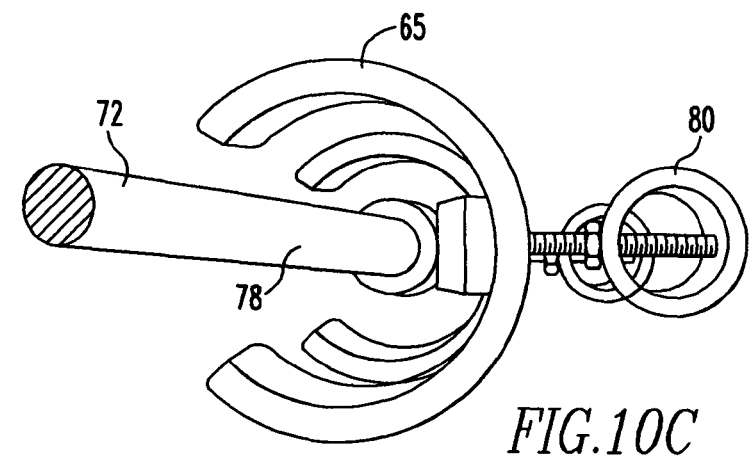
FIG. 10c is a front axial schematic view of the FIG. 10b hip mold central reinforcement member with two spaced apart, segment joinder clips.
Figure 12A:
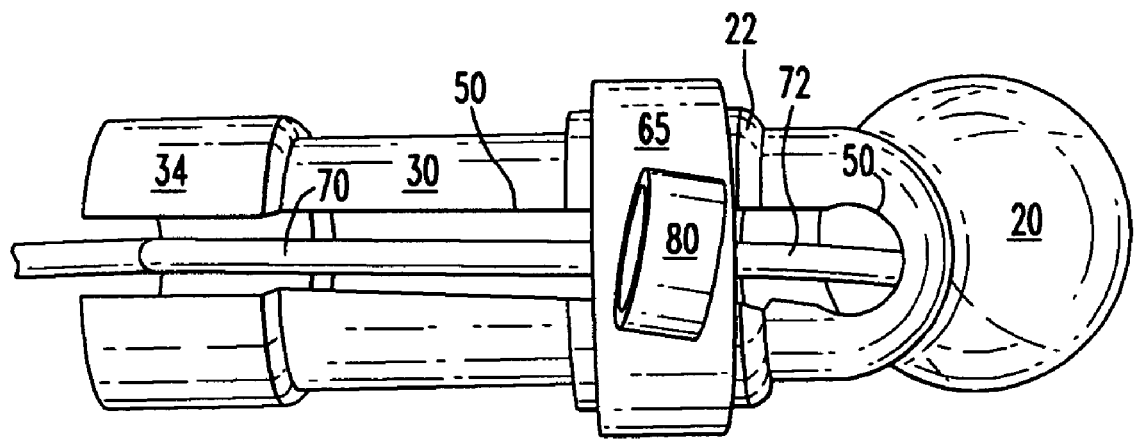
FIG. 12a is a top schematic view of a hip head and connector segments joined together with a reinforcement member and one segment joinder clip partially installed in same.
Figure 12B:
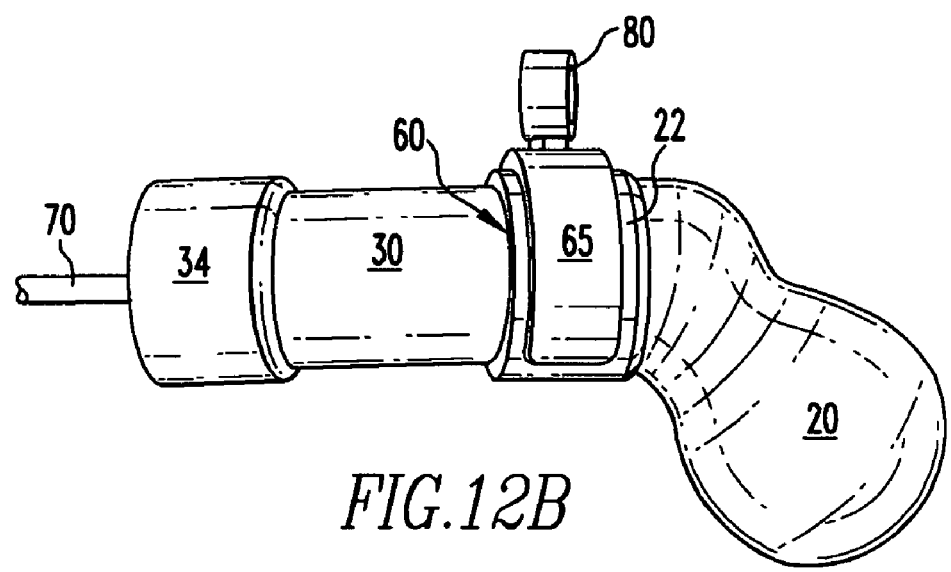
FIG. 12b is a right side schematic view of the FIG. 12a joined hip head and connector segments with central reinforcement member and one segment joinder clip therein.
Figure 13:
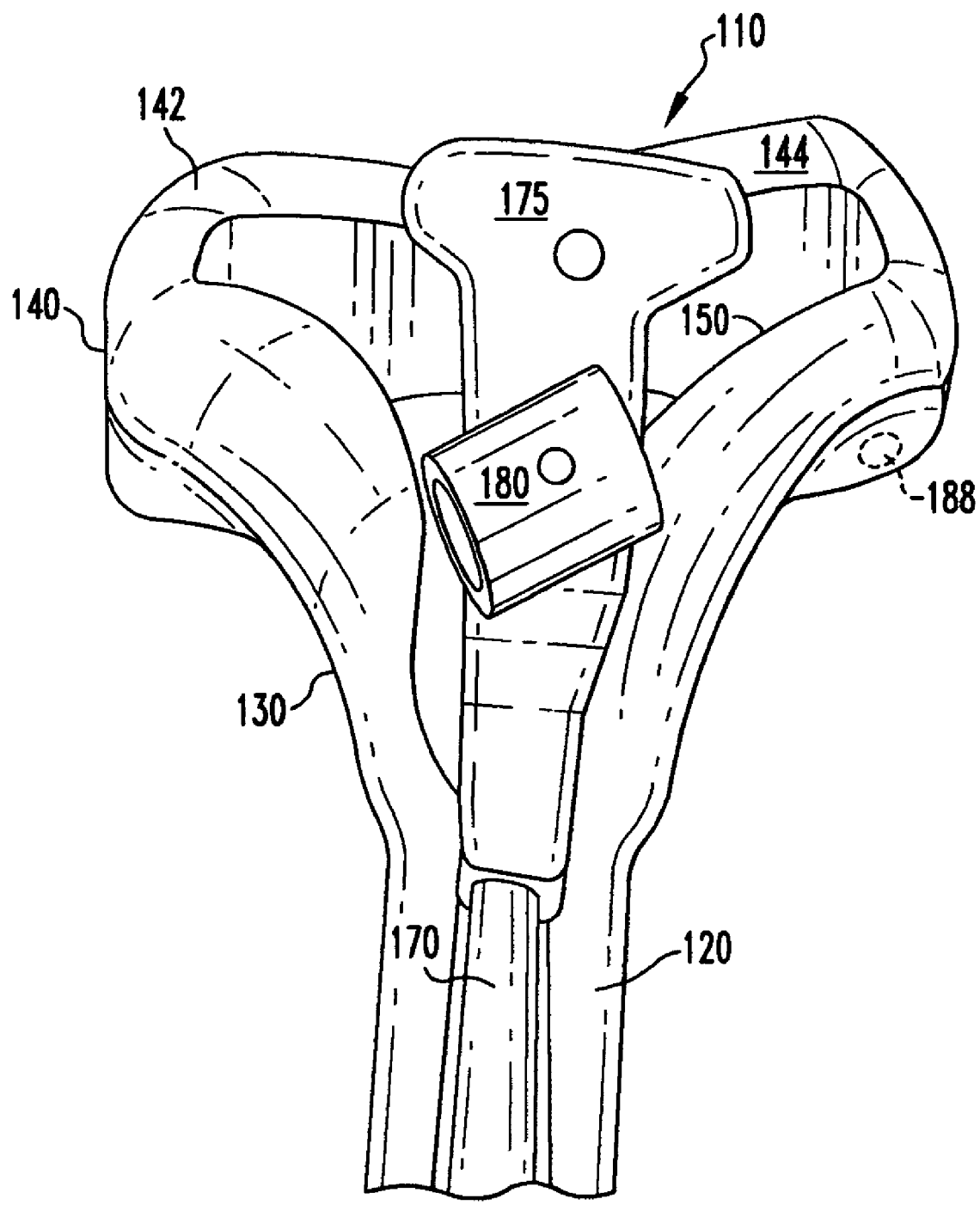
FIG. 13 is a top schematic view of a fully assembled, small femoral knee mold according to another preferred embodiment of this invention.
Figure 14A:
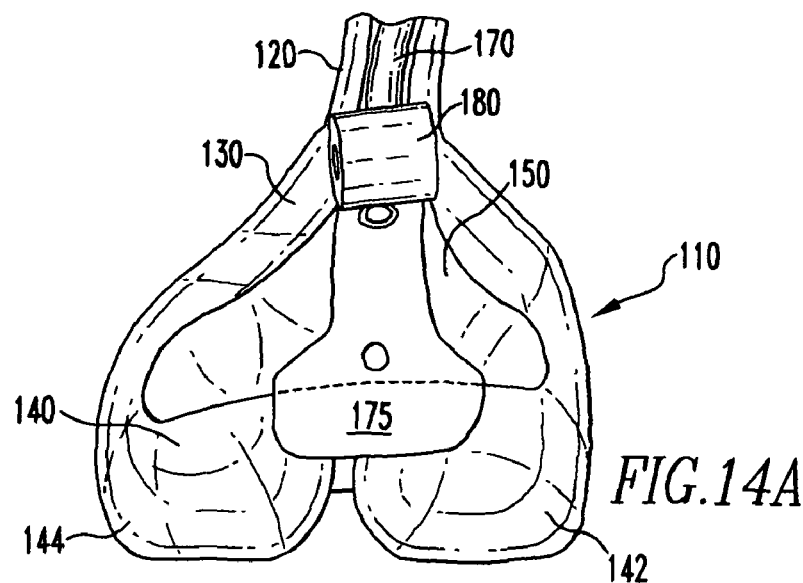
FIG. 14a is a top view of a fully assembled, large femoral knee mold according to another preferred embodiment.
Figure 14B:
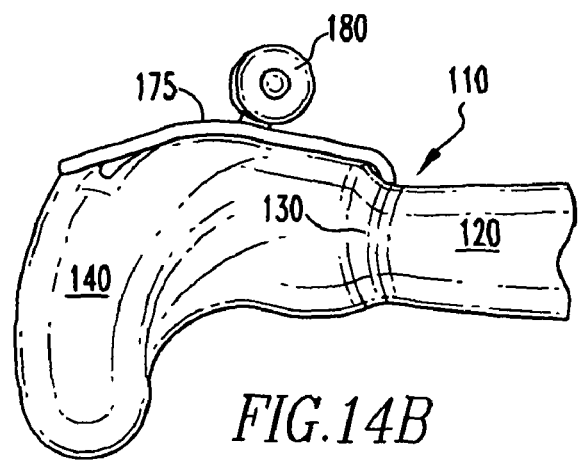
Figure 14C:
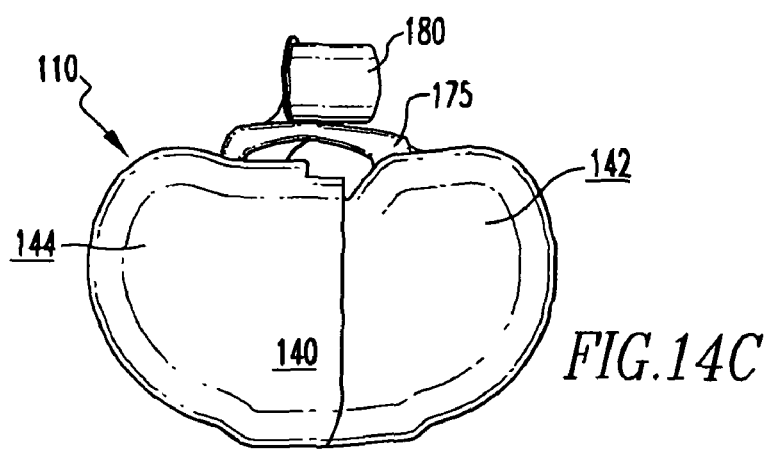
Figure 15A:
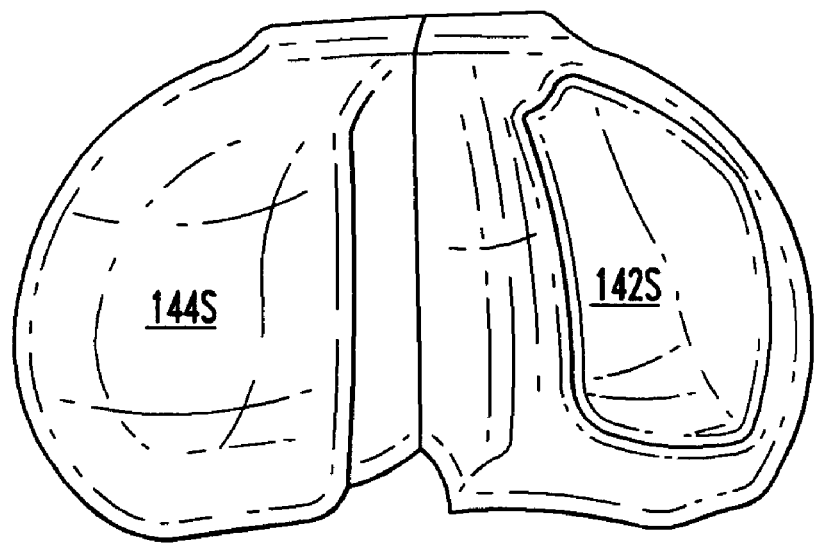
FIG. 15a is a front axial schematic view of a small femoral knee segment according to the invention.
Figure 15B:
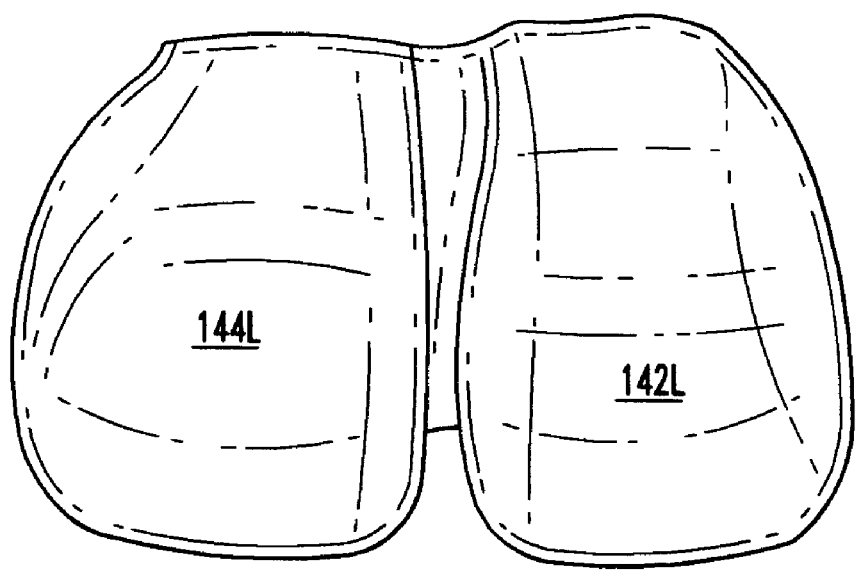
Figure 16A:
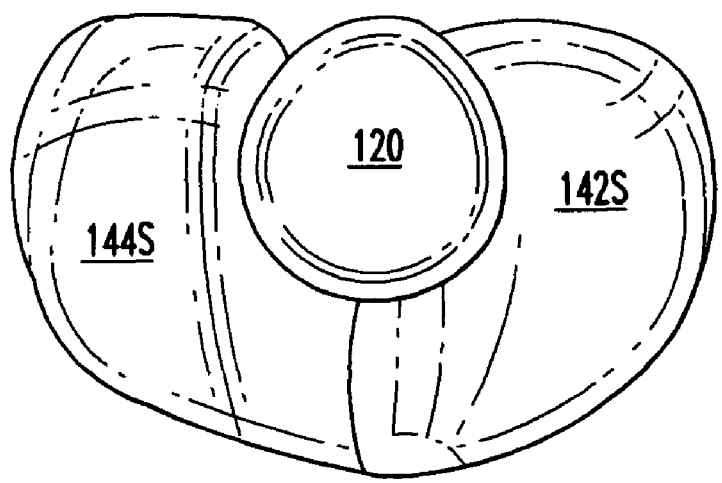
FIG. 16a is a rear axial schematic view of a small femoral knee segment according to the invention.
Figure 16B:
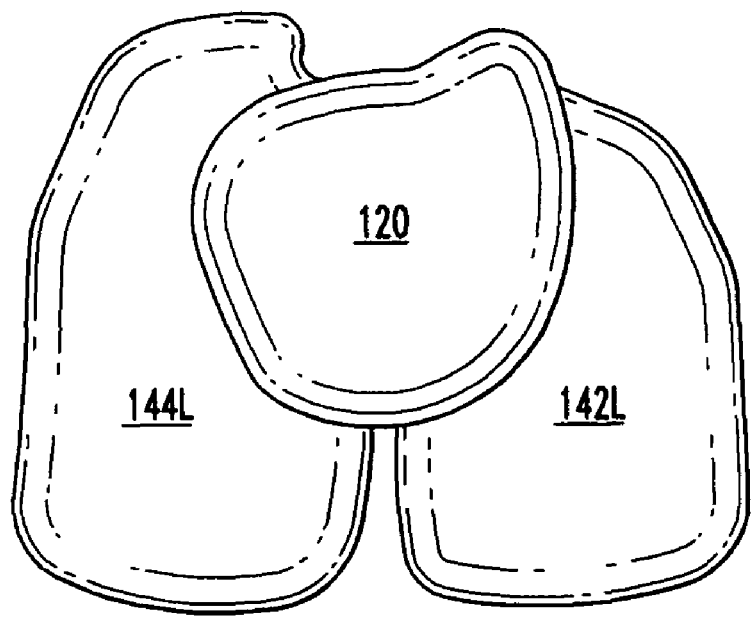
Figure 17A:
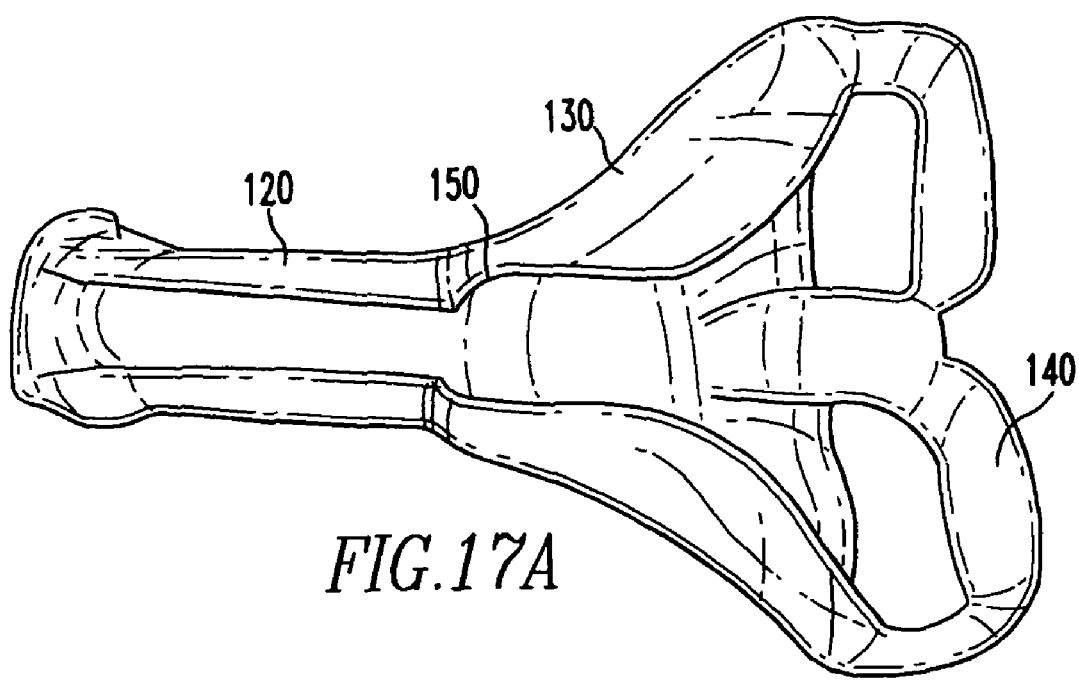
FIG. 17a is a top, channel schematic view of a large femoral knee segment according to one embodiment of the invention.
Figure 17B:
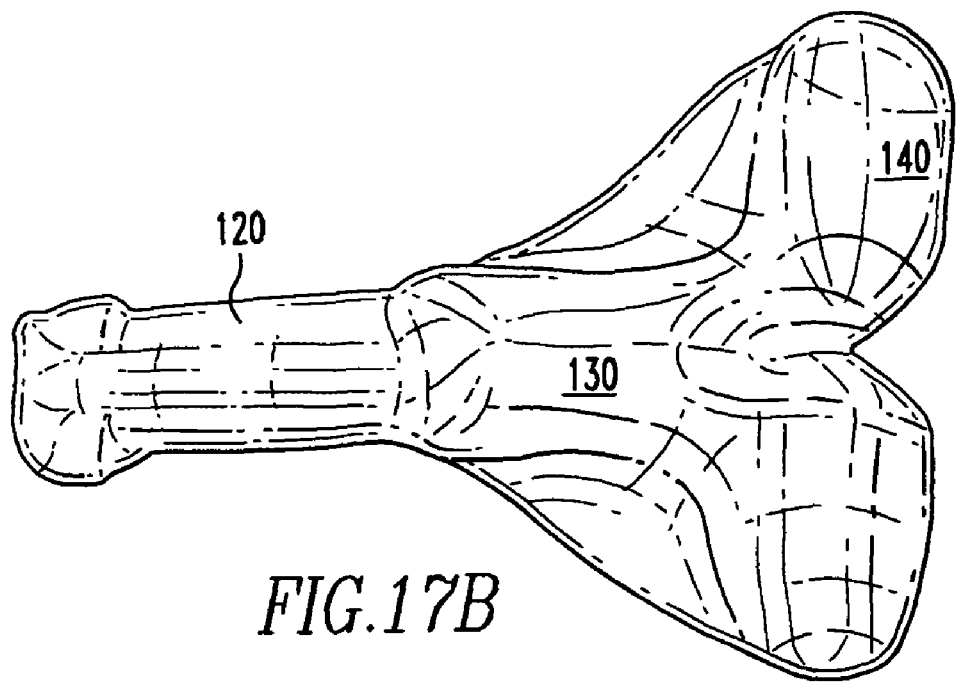
FIG. 17b is a bottom schematic view of the FIG. 17a large femoral knee segment.
Figure 18A:
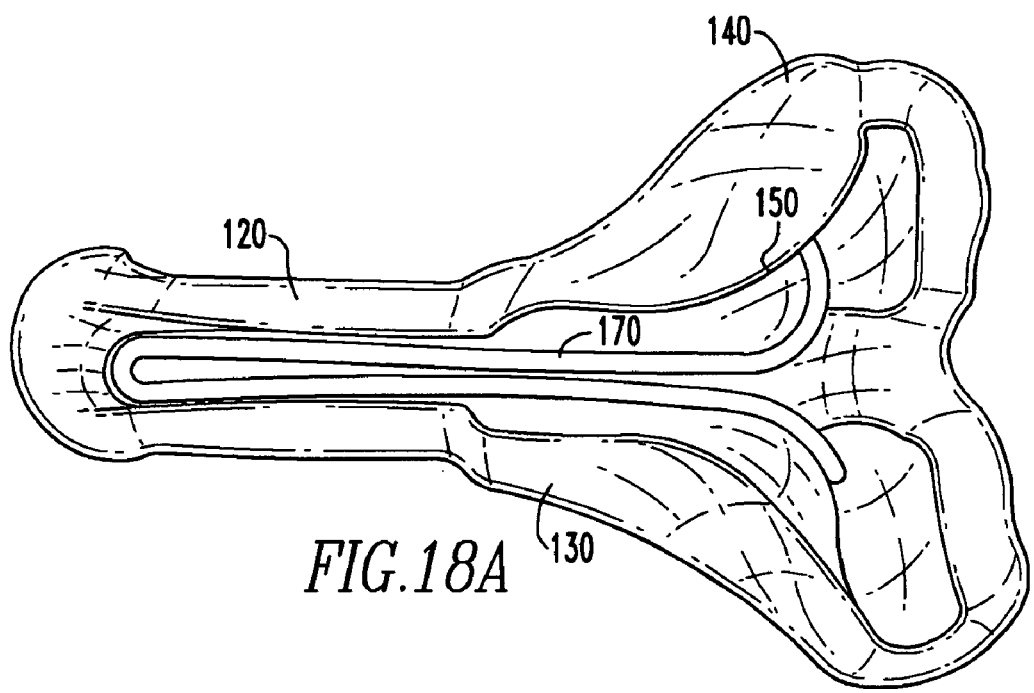
FIG. 18a is a top schematic view of a small femoral knee mold segment with a reinforcement member merely laid in same.
Figure 18B:
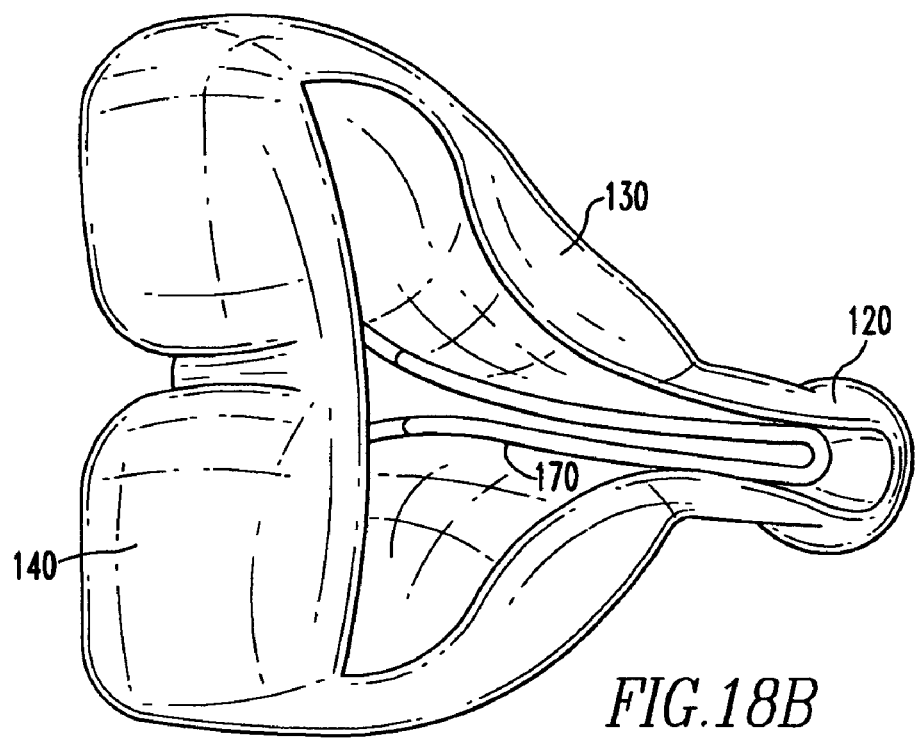
Figure 19A:
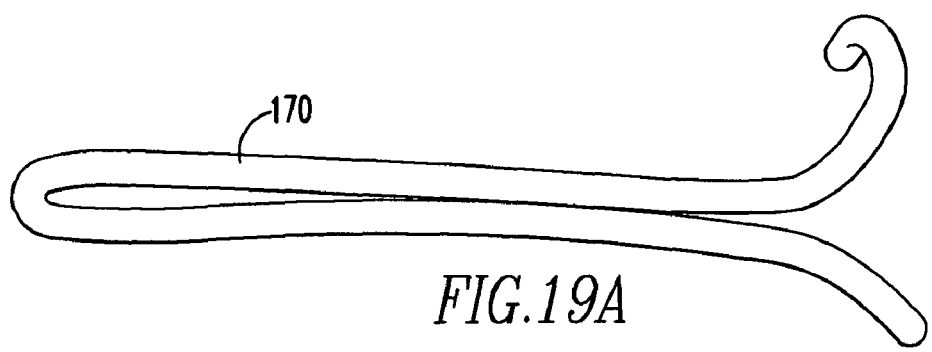
FIG. 19a is a top schematic view of one embodiment of reinforcement member for a small femoral knee segment according to the invention.
Figure 19B:
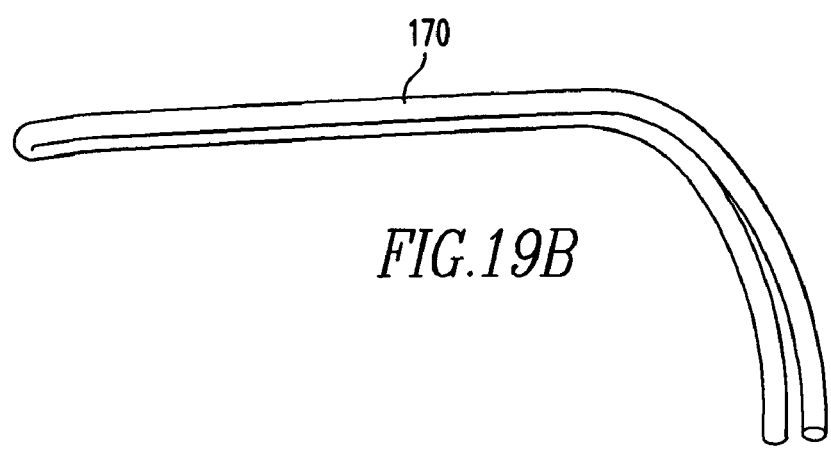
FIG. 19b is a right side schematic view of the FIG. 19a femoral knee segment reinforcement member.
Figure 19C:
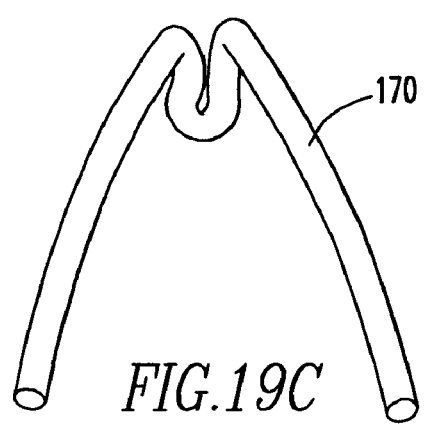
FIG. 19Oc is a front axial schematic view of the FIG. 19a reinforcement member.
Figure 20A:
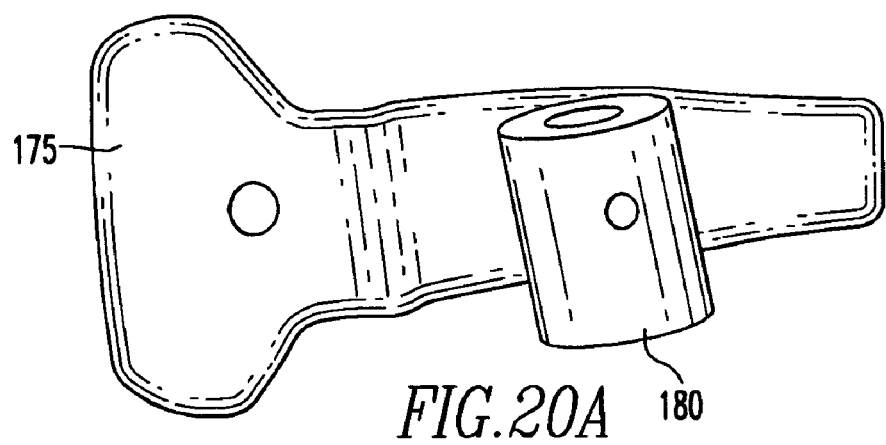
FIG. 20a is a top schematic view showing one embodiment of femoral knee segment reinforcement member holder per this invention.
Figure 20B:
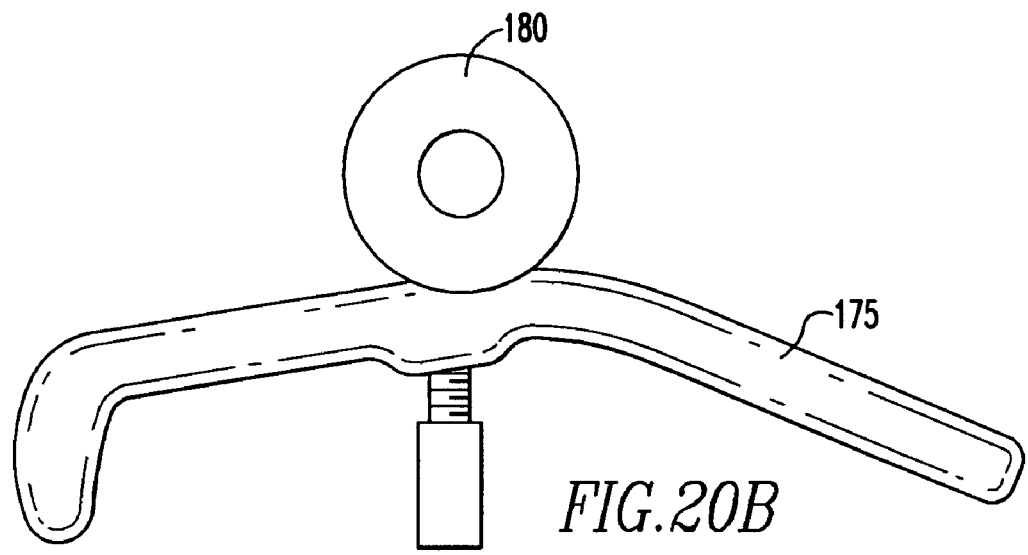
FIG. 20b is a side schematic view of the FIG. 20a mold segment reinforcement member holder.
Figure 21A:
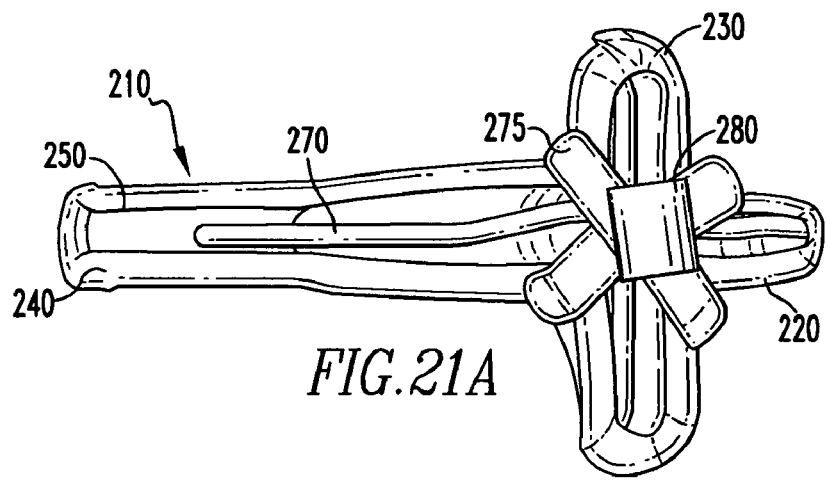
FIG. 21a is a top schematic view of a fully assembled, tibial knee mold according to another preferred embodiment of the present invention.
Figure 21B:
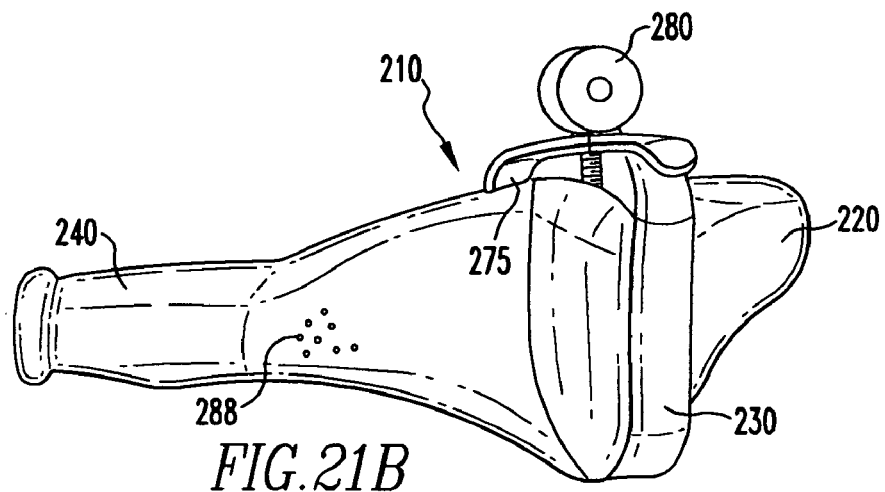
Figure 21C:
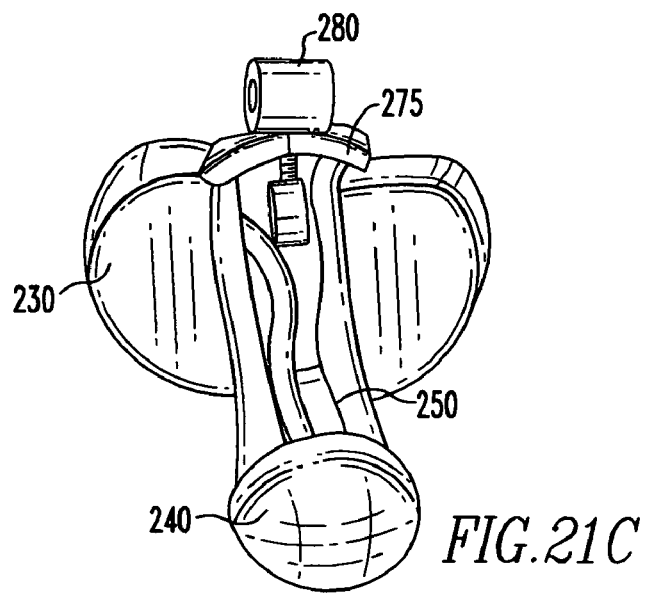
Figure 22A:
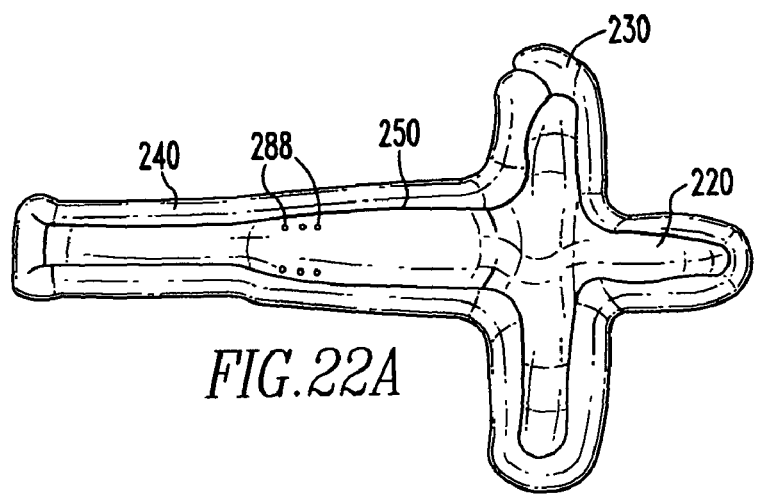
FIG. 22a is a top schematic view of a stemmed, tibial knee segment according to the present invention.
Figure 22B:
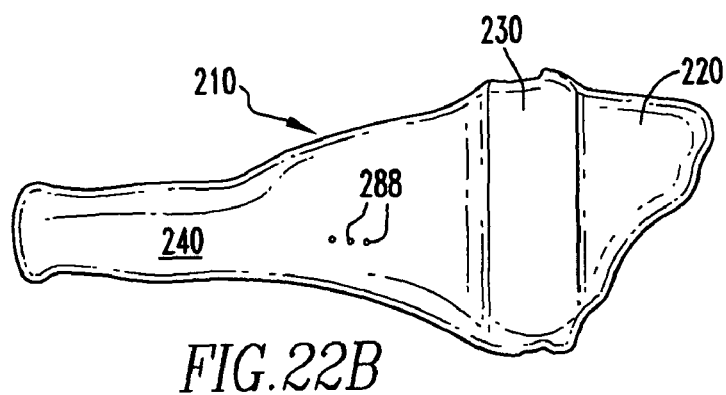
Figure 22C:
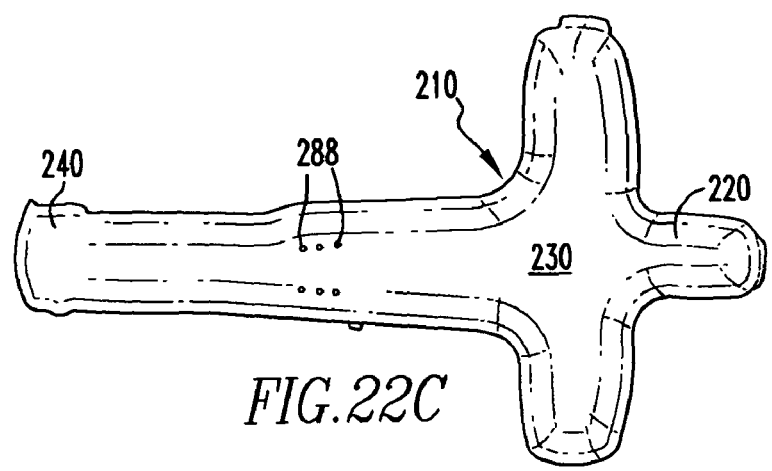
FIG. 22c is a bottom schematic view of the FIG. 22a stemmed, tibial knee segment.
Figure 23A:
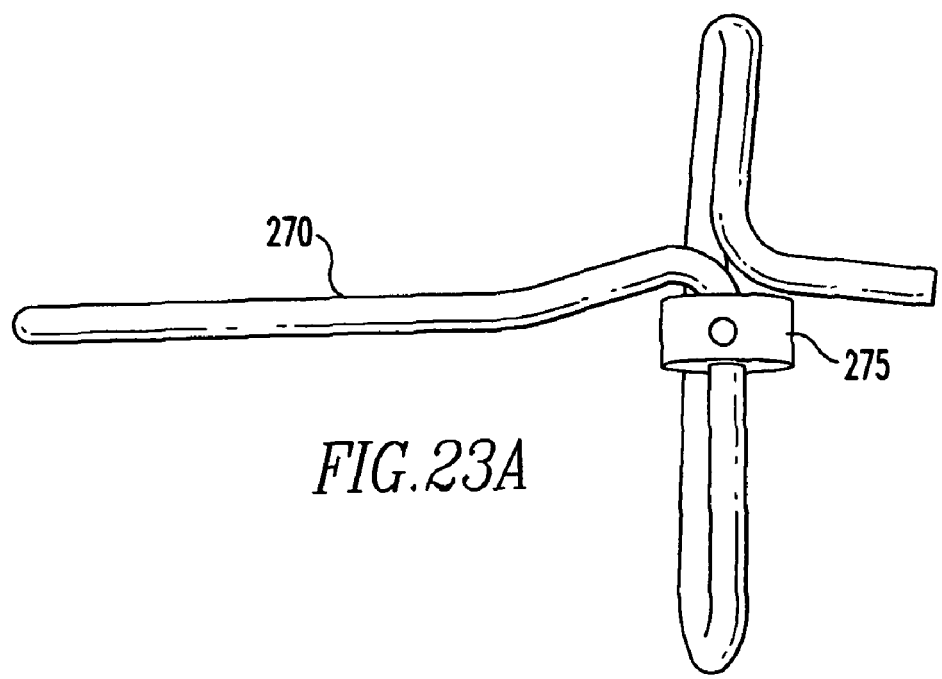
FIG. 23a is a top schematic view of one embodiment of reinforcement member for a stemmed, tibial knee segment according to the invention.
Figure 23B:
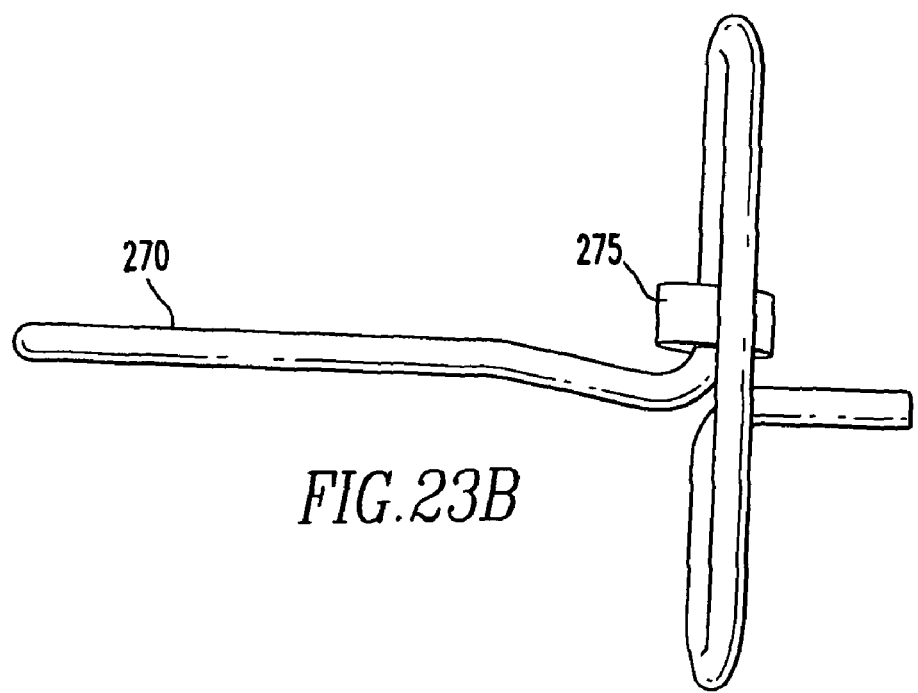
FIG. 23b is a bottom schematic view of the FIG. 23a tibial knee segment reinforcement member.
Figure 23C:
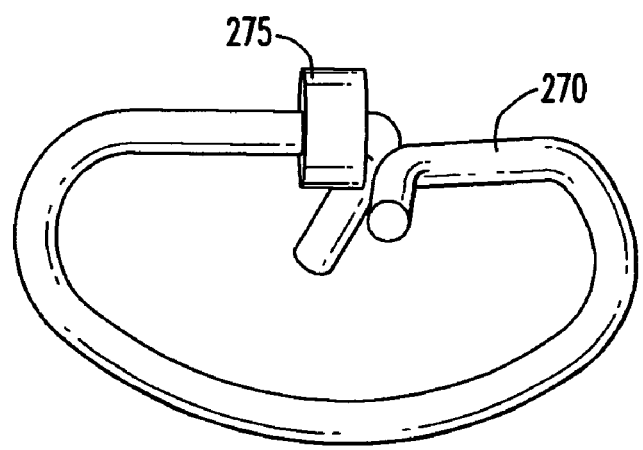
FIG. 23c is a front axial schematic view of the FIG. 23a reinforcement member.
Figure 23D:
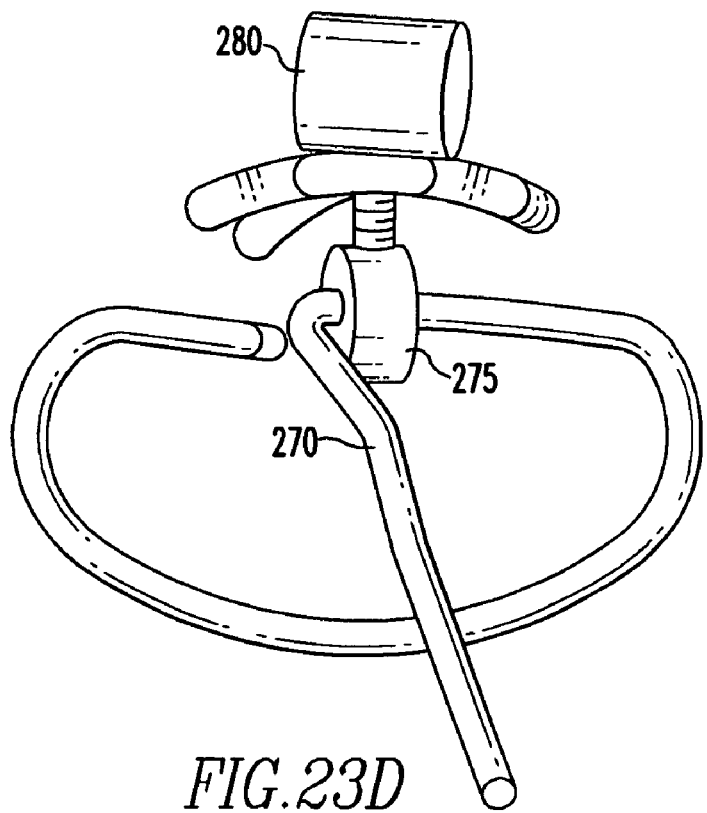
FIG. 23d is a rear axial schematic view of the FIG. 23a reinforcement member.
Figure 24A:
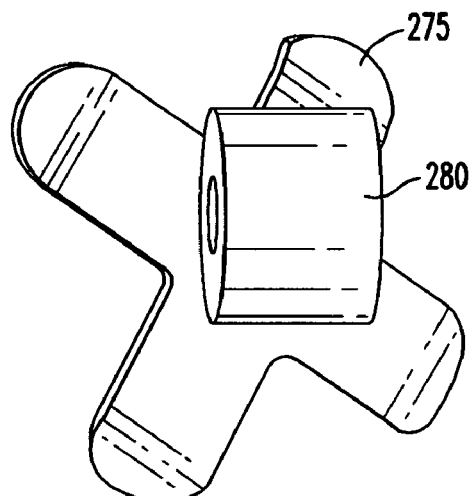
FIG. 24a is a top schematic view of one embodiment of tibial knee segment reinforcement member holder according to the invention.
Figure 24B:
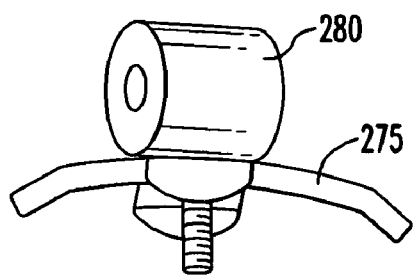
Figure 24C:
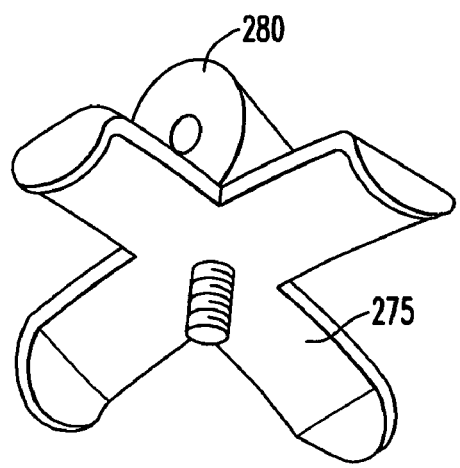
Figure 25A:
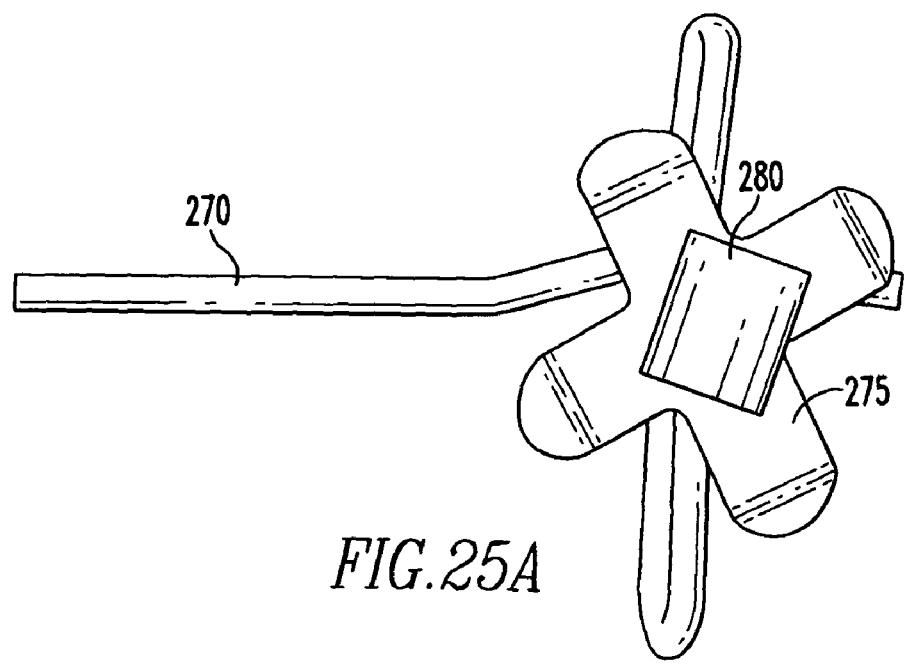
FIG. 25a is a top schematic view of a tibial knee segment reinforcement member with the reinforcement member holder positioned thereon.
Figure 25B:
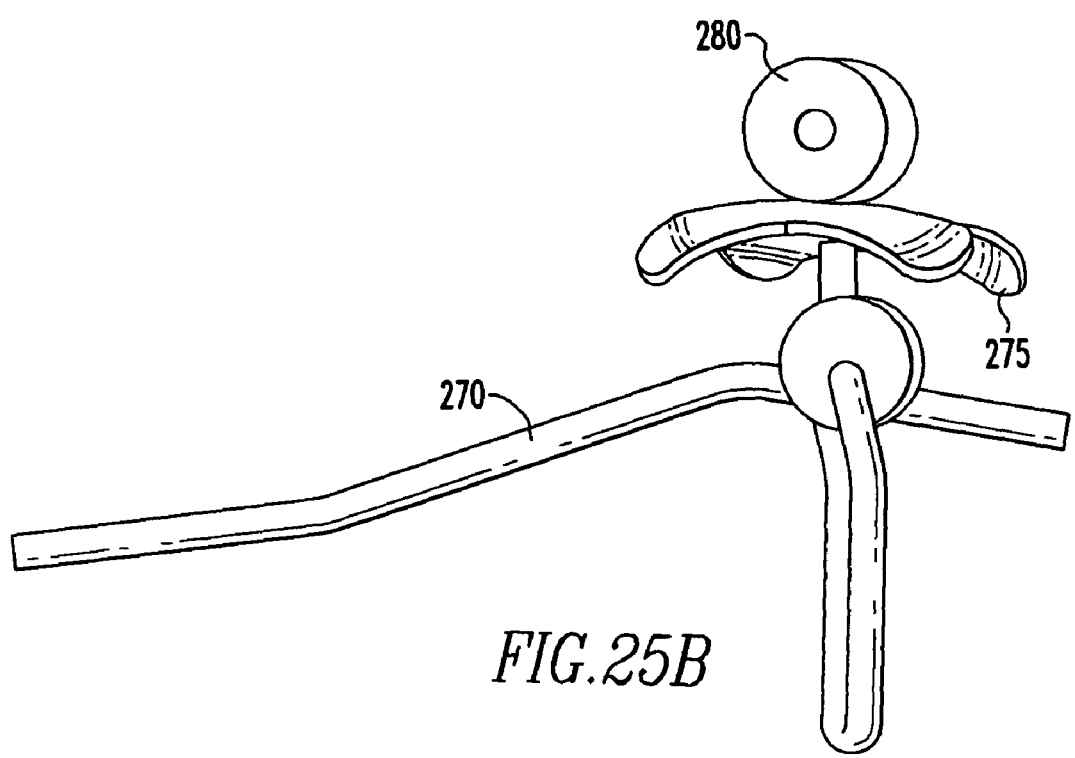

The following description of preferred embodiments is merely exemplary and not intended to unnecessarily limit the invention or its application and/or end uses. Moreover, while the present invention is described below with reference to cement molds for hip and knee joints, it would be appreciated by those skilled in the art that other applications of this method and mold system be used to make other temporary orthopedic surgical parts.

The preferred methods of making mold segments by this invention allow surgical staffs to keep low inventories of segmented mold parts on hand. For a typical temporary hip replacement surgery, for example, operating rooms would need to have access to only twelve varieties of hip head sizes, two different stem lengths and five stem diameters along with 1-2 cm connector body increments (five in total) for a total hip inventory of roughly twenty segmented parts. Many of those same parts have applicability in some knee replacement surgeries. For the latter, an additional inventory of knee-specific, mold segments would require keeping on hand: three standard femoral and tibial sizes; three modular femoral and tibial sizes, along with the two stem lengths and five diameters affiliated with typical hip joint implant surgeries.

With this modular mold segmenting approach, still other mold shapes can be assembled for making possible ankle, elbow and/or shoulder temporary bone implants. To the bone cements added to such molds, surgeons can incorporate a variety of "off label" antibiotics. And the mold components of this invention need not be translucent like the mold shapes required in U.S. Pat. Nos. 6,155,812 and 6,361,731. On the contrary, it is preferred that the exteriors of these mold segments be kept opaque for better contrast with the bone cement that passes through little apertures in critical filling areas of a given mold segment. In that matter, the cement pourer/mold filler can visually determine when sufficient amounts of bone cement has flowed into (and perhaps even a little bit through) those critical mold filling regions (i.e., where a leftover air pocket along a long sidewall, or critical curve, might lead to cracking or crack expansions under certain stress conditions).

As the method of this invention is only used to make temporary implants, even if the patient's use of same can extend for 6 to 9 months on occasion, it is not especially critical that the resultant end product have an exterior surface that is wholly flaw free. The fitting of hip, knee and other replacement joints need not be 100% perfect. They are, indeed, only temporary until the patients can be re-implanted with a permanent prosthetic. Should the exteriors to these mold segmented-derived implants have superficial cracking or pitting, in non-stress bearing areas, defects such as those can be kept "uncorrected"; or they can be aesthetically patched (i.e., spackled) using the typical cement mold sculpting instruments found in many surgical operating rooms today.

While the modular mold segments of this invention include an open channel or vessel through which bone cement is poured, and through which a reinforcement member is fitted during the mold manufacturing process, these molds do not require any air venting ports like those shown and described by Smith et al. Nor does the present method of mold manufacture hereby require footplates for leveling a mold during cement filling. A vacuum drawn, holding bag is sufficient substitution for leveling these molds while liquidous cement is poured (or ladeled in) and allowed to chemically cure. Alternatively, the cements of these molds can be mixed in small quantities and added to a caulking-style cement gun. Either way, it is preferred that at least some initial quantity of bone cement be added to the combination of connected mold segments before the reinforcement member gets added through the channels and into the mold segments proper. When time is not of the essence, it is even conceivable to add bone cement to the molds of this invention in discretely distinct layers.

Referring now to FIGS. 1a through 12b, there is shown a temporary hip mold manufacturing process and system according to this invention. The hip mold, generally 10, holds bone cement like PMMA deposited into same for curing to make a temporary hip implant. More particularly, the mold segments that are joined together for making hip mold 10 include a top/hip head segment 20, intermediate connector segment 30 and a lower or bottom stem segment 40. These segments are currently made from a polyethylene material that is readily tearable yet sufficiently stiff so that the mold will not sag or deform during normal handling and/or setup. It may be possible, near term, to replace the aforementioned polymeric material with an even more "disposable" model made from pretreated/waxed cardboards or the like. But until then, one preferred polyethylene suitable for injection or vacuum molding into preset mold segment shapes hereby is a line of polymeric sold by Dupont as Surlyn®. Whichever model materials are selected, it is critical that they remain compatible with the bone cements concocted for pouring into mold segments made therefrom; yet be complementary to the one or more antibiotics to be added to the PMMA or the like during temporary implant manufacturing hereby. Ideally, the polymeric selected should be opaque for contrasting with the milky white bone cement that will pass (or "ooze") through tiny mold-filling apertures in only select areas of certain mold segments for quickly and easily, indicating to the mold filler when sufficient quantities of bone cement have been poured into, and a little bit through, those given mold shapes. For ease of illustrating various aspects of this invention, however, the mold segments shown throughout these early stage figures and all made from a semi-transparent mold material.

In an alternative embodiment, a plurality of mold segments could be fashioned from an ultra thin, polymeric similar to the consistency of a pill blister pack, i.e. the type of packaging having a foil sealed end for encapsulating the pills inside. In this alternative, final implant molds would be identical in shape to the molds discussed above and while not foil backed per se, a non disposable rigid cradle design could essentially hold (or "hug" these molds for helping them maintain their necessary shapes due to an otherwise flimsy design employing ultra thin polymerics. From this arrangement, molds could be presses from/pushed out of a "blister pack" as needed.

For making a temporary hip implant by the present invention, it is first necessary for the surgeon or another member of the surgical team to first "size" the patient using a set of trial fittings (not shown) for approximating which sizes of mold segments to first assemble together. Separately, or even concurrent with initial sizing, one or more packets of bone cement powder are next mixed together with the preferred antibiotic(s) for the patient's particular infection-fighting needs. One preferred line of cement products is the polymethyl-methacrylate (or PMMA) commonly sold under such present day trade names as CMW1, CMW2, CMW3, Zimmer Dough Type, or Zimmer LVC. An alternative cement to use is the MMA-styrene copolymer cement made as sold as Howmedia Simplex P or Zimmer Osteobond. Yet another is the MMA-methyl acrylate copolymer variety sold under the Palacos R label. One representative antibiotic suitable for use the foregoing cement lines is a gentamicin. After the one or more antibiotics are blended in, the ampoule of active liquid monomer gets added to the aforementioned and preferably stirred to accelerate the start of cement curing to a limited degree. Thereafter, the fully mixed bone cement is poured into a duly held hip mold 10, or to a lesser degree injected from a cement gun (not shown) into the channel 50 running concurrently through hip head segment 20, connector segment 30 and stem segment 40.

Figure 27:
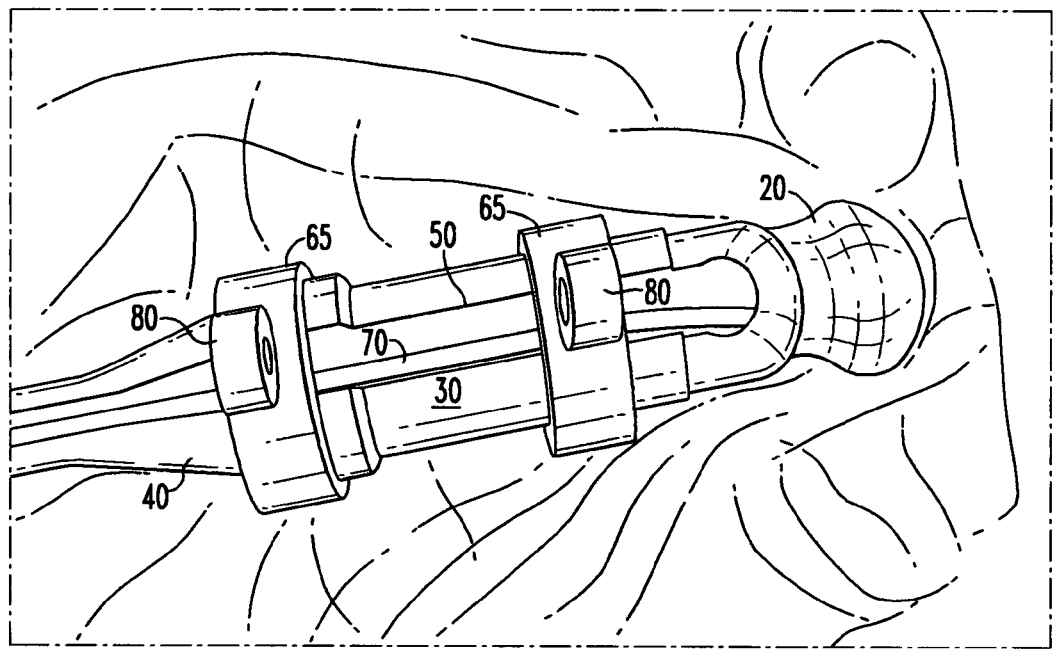
FIG. 27 is a top schematic view showing an assembled hip mold in vacuum drawn, packing (with insulation removed for illustrative purposes) for holding during cement filling and curing.

While the mold segments used to make hip mold 10 are intentionally meant to vary in hip head and stem diameter, or overall stem length (the connectors are purposefully varied for custom selection of the overall mold lengths needed for implant manufacture hereby), it is nevertheless a critical aspect of this invention that all the segment join together. The open end to the hip head segment 20 should have a female collar 22 sized to fit over and about, but otherwise snugly against the smaller male end 32 to connector segment 30. At the reverse end of same, connector segment will have its own female collar end 34 for accommodating the forward leading male tip 42 to stem segment 40. But throughout all of these various segments and segment connector geometries, channel 50 extends commonly throughout the mold top proper. It may happen that the common channel 50 for hip head segment 20 does not at first align with the channel atop connector segment 30. But by the simple rotational, universal fit design of joinder areas 60, a slight clockwise (or counterclockwise) rotation of the one mold segment relative to its neighbor should result in all the channels of the respective mold segmented parts being in full alignment prior to positioning in the vacuum drawn holder (see generally, FIG. 27) during typical mold filling. In some instances, it may be necessary to hold certain combinations of mold segments together manually. For such an occasion, one or more joinder clips 65 may be positioned along channel 50 over one or more segment joinder areas 60.

Once the mixture of bone cement (and antibiotic additive(s) if desired) is poured into hip mold 10 has sufficiently cured, a member of the surgical team can extract the implant from this mold form, usually by cutting or tearing away sections of the assembled mold exterior. To better expedite mold removal at the end of this implant-making process, certain sections of certain mold segment exteriors can be provided with pre-score lines 68.

Through the channel 50 along hip head segment 20, connector segment 30 and stem segment 40 of hip mold 10, a central reinforcement member (or metal rebar) 70 is fitted, preferably after a first quantity of bone cement has been poured to for a base or bed on which rebar 70 may rest. In this particular example, rebar 70 is made from steel and purposefully pre-curved at section 72 for better positioning in the hip head and remaining mold segments making up hip mold 10. For better holding of rebar 70 in hip mold 10 while the rest of the bone cement is poured to fully encompass the reinforcement member and otherwise substantially fill the mold to the top of channel 50, there are situated a plurality of reinforcement member holders, or centralizers 75. In some instances, it may be appropriate to further add one or more spacers 78 along the shaft of rebar 70. One or both centralizers 75 or spacers 78 may include a threaded handle portion 80. That handle alternative allows for better tightening (or downwardly forcing) of the rebar into a hip mold 10 nearly fully filled with still semi-liquidous bone cement. By such handle tightening, alone or in combination with the application of greater pressures along opposite ends of rebar 70, the reinforcement member pushes cement into all remaining empty crannies in the mold segments, necessarily even causing some excess bone cement to ooze, or otherwise pass through and fully or partially fill the plurality of mold segment apertures 88 positioned in only key (i.e. more critical) filling areas of the segments making up hip mold 10. At the end of cement additions to this mold, it is most preferred that no areas of rebar 70 be contacting a mold interior sidewall, or otherwise extend outwardly beyond the temporary implant exterior. True, the implant itself has antibiotics laced throughout its body proper for subsequent, purposeful leaching into the patient over time. But it would be preferred that no metal sections of rebar be left exposed as a possible bacteria colonization site going forward.

After its manufacture by the method steps set forth above, the resultant temporary hip implant may be engaged in the intramedullary canal of a patient's femur region. The distal stem of that implant is meant to fit snugly in the patient's intramedullary canal while an articulating head couples to a neck for rotatably engaging with the acetabulum. This will enable the distended joint subsequently reengage with the hip giving the patient at least some, limited degree of non-load bearing movement until the patient's full prosthetic device is ready for substituting for this antibiotic delivering temporary alternative.

Turning now to FIGS. 13 through 21b, there is shown a system and method for making a femoral knee mold 110 from which a femoral knee implant 199 would be made according to the present invention. The major segments comprising that mold are a first anterior portion 120, an intermediate distal portion 130 and a posterior portion 140 which when combined result in the manufacture of an implant having substantially two condyle sections 142 and 144.

In the channel 150 along the top of femoral knee mold 110, there is provided an area for accepting a correspondingly shaped reinforcement member 170. To best hold that member in place while bone cement is poured about this mold segment, there are provided one or more, uniquely shaped rebar holders or centralizers 175. A plurality of apertures 188 can be positioned through the exterior of one or more sections of this femoral knee mold 110 for visually indicating to the mold filler when sufficient quantities of bone cement have caused at least some portion of milky white bone cement to at least partially pass through these apertures 188 indicating the relative fullness of the mold proper. The resultant temporary implant made from this mold segment, available in more than one basic femoral knee bone size and shape, can best be seen on the right side of accompanying FIG. 26.

The femoral knee implant is not a typical stand alone surgical procedure, however. When the femoral knee is being removed, most often the tibial knee bone is also being replaced albeit, at first, on a temporary basis. For those situations, a temporary tibial knee implant 299, as best seen in the left side of accompanying FIG. 26, can be made according to the present invention. Referring now to FIGS. 21a through 25b, the tibial knee mold 210 somewhat resembles a cross having a tibial top region 220, with a central plate region 230 between the tibial top and a lowermost tibial stem region 240. The channel 250 atop all three regions, like the other multisectional mold segments described above is the main means by which liquidous bone cement gets delivered into tibial knee mold 210. With one or more set of apertures 288 in key filling areas of this mold 210, the person pouring bone cement into the vacuum-held mold can readily determine when sufficient quantities of cement added through tibial channel 250, to surround reinforcement member 270 without interfering with the uniquely shaped centralizer/holder 275 that keeps reinforcement member away from all interior sidewalls of tibial knee mold 210. Note especially, the preferred configuration of reinforcement member 270 which, through a series of twists allows it to made as essentially a one-piece unit.

Figure 26:
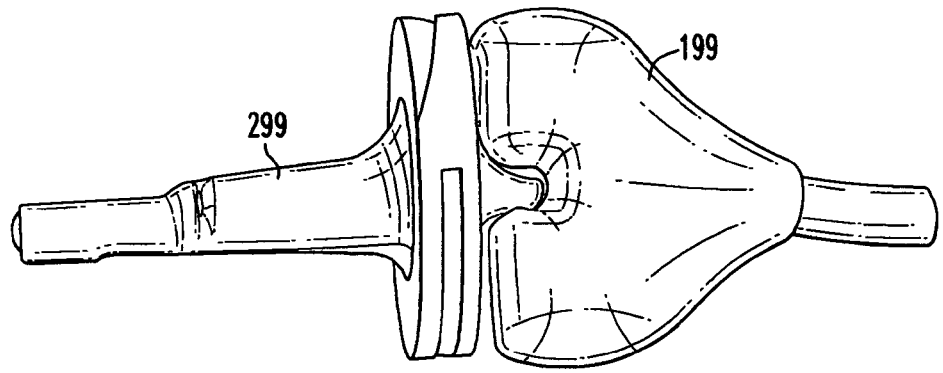
FIG. 26 is a side schematic view of the femoral and tibial knee implants made from mold similar to the ones shown in FIGS. 13 and 21 respectively.

When the bone cement has duly cured, and the mold proper is removed, the resultant combination of femoral and tibial knee implants has the general appearance of a prosthetic device like the product best seen in FIG. 26. In some instances, it may prove beneficial to make various mold segments in half-sections that would be connected by known "butterfly hinge" mechanisms. Such mold half connections are easier to initially assemble, and better still, remove from an implant after the bone cement has sufficiently cured.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A method of forming for a patient an adjustable length, surgical implant made from a bone cement, said method comprising:
    (a) connecting three or more disposable mold segments to approximate the length of surgical implant needed for the patient, each mold segment being made from an opaque material and having an elongated channel through which the bone cement will be fed and an implant reinforcement member will be inserted after partial mold filling with the bone cement;
    (b) aligning the elongated channels of adjacent connected mold segments;
    (c) positioning at least one mold centralizer on the reinforcement member sized for fitting within the connected mold segments;
    (d) mixing the bone cement;
    (e) pouring a first quantity of the bone cement through the aligned, elongated channels of and into the connected mold segments;
    (f) fitting the reinforcement member and mold centralizer through the aligned, elongated channels for substantially centering the reinforcement member within the connected mold segments before they are completely filled with the bone cement and fully encompass the reinforcement member therein;
    (g) pouring a second quantity of the bone cement about the reinforcement member to substantially fill the connected mold segments;
    (h) curing the bone cement; and
    (i) removing the mold segments from about the cured bone cement to form the surgical implant that was adjusted in length for the patient.

2. The method of claim 1 which further comprises adding antibiotic to the bone cement during the mixing step.

3. The method of claim 1 which further comprises loading the bone cement in an applicator after the mixing step.

4. The method of claim 1, wherein certain areas of said mold segments include a plurality of apertures through which excess bone cement will pass for indicating substantial filling of those mold segment areas.

5. The method of claim 1, wherein removing step (i) comprises: cutting the mold segments away from the surgical implant.

6. The method of claim 1 which further comprises positioning connected mold segments in a holding apparatus before the first pouring step.

7. The method of claim 1, wherein the implant is used for replacing an articular joint in the patient.

8. The method of claim 1, wherein the implant is used for replacing one or more hip, knee, leg or ankle bones in a patient.

9. The method of claim 4 which further comprises removing excess bone cement that has passed through the mold segment apertures.

10. The method of claim 5, wherein an exterior of one or more mold segments is pre-scored.

11. The method of claim 6, wherein the holding apparatus comprises vacuum extraction packing and an insulated cover.

12. A method of forming an articular joint implant customized in length for a patient, said articular joint implant being made from a mixture of bone cement with one or more antibiotics, said method comprising:
    (a) interconnecting appropriate lengths of opaque mold segments to approximate the length of articular joint implant needed for the patient, at least some of said opaque mold segments having: (i) a slotted channel through which the mixture will be fed and through which a central reinforcement member will be inserted after the opaque mold segments are partially filled with the mixture; and (ii) a plurality of apertures through which excess mixture will pass for indicating sufficient mixture filling into that opaque mold segment;
    (b) aligning the slotted channels of adjacent opaque mold segments;
    (c) positioning a plurality of mold spacers on the reinforcement member;
    (d) inserting the reinforcement member through the aligned slotted channels and into the connected opaque mold segments;
    (e) making the mixture of bone cement with one or more antibiotics;
    (f) holding the connected opaque mold segments substantially level in a holding apparatus;
    (g) pouring the mixture through the slotted channels and into the connected opaque mold segments until excess mixture has passed through a sufficient quantity of the mold segment apertures;

(h) curing the mixture within the connected opaque mold segments; and (i) removing the connected opaque mold segments from about the cured mixture to form the articular joint implant customized in length for the patient.

13. The method of claim 12, wherein the articular joint implant is selected from the group consisting of a hip, knee, leg or ankle bone.

14. The method of claim 2, wherein at least some of the mold segment exteriors are pre-scored.

* * * * *